(12) United States Patent
Brill et al.

(10) Patent No.: US 10,842,989 B2
(45) Date of Patent: Nov. 24, 2020

(54) SYSTEM TO IMPROVE A SPINAL CORD STIMULATION MODEL BASED ON A PHYSIOLOGICAL MIDLINE LOCATION

(71) Applicant: Boston Scientific Neuromodulation Corporation, Valencia, CA (US)

(72) Inventors: Natalie Brill, Sherman Oaks, CA (US); Raul Serrano Carmona, Los Angeles, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 124 days.

(21) Appl. No.: 16/135,976

(22) Filed: Sep. 19, 2018

(65) Prior Publication Data

US 2019/0134383 A1  May 9, 2019

Related U.S. Application Data

(60) Provisional application No. 62/583,332, filed on Nov. 8, 2017.

(51) Int. Cl.
 A61N 1/05 (2006.01)
 A61N 1/36 (2006.01)
 (Continued)

(52) U.S. Cl.
 CPC ............ A61N 1/0553 (2013.01); A61B 5/407 (2013.01); A61N 1/36062 (2017.08);
 (Continued)

(58) Field of Classification Search
 CPC .... A61B 5/0488; A61B 5/407; A61N 1/0553; A61N 1/36062; A61N 1/36071;
 (Continued)

(56) References Cited

U.S. PATENT DOCUMENTS

| 5,814,092 A | 9/1998 | King |
| 6,078,838 A | 6/2000 | Rubinstein |

(Continued)

FOREIGN PATENT DOCUMENTS

| EP | 2709721 | 9/2016 |
| WO | 2006/029090 | 3/2006 |

OTHER PUBLICATIONS

International Search Report and Written Opinion regarding corresponding PCT Application No. PCT/US2018/051786, dated Dec. 10, 2018.

(Continued)

*Primary Examiner* — Gary Jackson
*Assistant Examiner* — Jonathan T Kuo
(74) *Attorney, Agent, or Firm* — Lewis & Reese, PLLC

(57) ABSTRACT

Techniques for determining the location of a physiological midline and utilizing the physiological midline location to improve a spinal cord stimulation model are disclosed. A first improvement constructs a target stimulation field along a line that is parallel with the determined physiological midline. An allocation of stimulation among the electrodes to mimic the target field is computed. A second improvement models a response of neural elements at evaluation positions that are parallel with the physiological midline based on the electric field that is generated for the computed allocation of stimulation among the electrodes. The stimulation amplitude is adjusted based on the neural element modeling to maintain stimulation intensity, and the stimulation amplitude and allocation of stimulation among the electrodes are compiled into an electrode configuration that is communicated to a neurostimulator.

20 Claims, 13 Drawing Sheets

(51) Int. Cl.

| | | |
|---|---|---|
| *A61N 1/375* | (2006.01) | |
| *A61B 5/00* | (2006.01) | |
| *G16H 40/63* | (2018.01) | |
| *A61N 1/372* | (2006.01) | |
| *G16H 50/50* | (2018.01) | |
| *A61B 5/0488* | (2006.01) | |

(52) U.S. Cl.
CPC ..... *A61N 1/36071* (2013.01); *A61N 1/36139* (2013.01); *A61N 1/36185* (2013.01); *A61N 1/375* (2013.01); *A61N 1/37247* (2013.01); *G16H 40/63* (2018.01); *G16H 50/50* (2018.01); *A61B 5/0488* (2013.01); *A61N 1/36157* (2013.01); *A61N 1/36171* (2013.01); *A61N 1/37241* (2013.01)

(58) Field of Classification Search
CPC ............ A61N 1/36139; A61N 1/36157; A61N 1/36171; A61N 1/36185; A61N 1/37241; A61N 1/37247; A61N 1/375; G16H 40/63; G16H 50/50
See application file for complete search history.

(56) References Cited

U.S. PATENT DOCUMENTS

| | | |
|---|---|---|
| 6,516,227 B1 | 2/2003 | Meadows et al. |
| 6,718,210 B1 | 4/2004 | Peckham et al. |
| 6,907,130 B1 | 6/2005 | Rubinstein et al. |
| 7,024,247 B2 | 4/2006 | Gliner et al. |
| 7,424,322 B2 | 9/2008 | Lombardi et al. |
| 7,450,992 B1 | 11/2008 | Cameron |
| 7,890,182 B2 | 2/2011 | Parramon et al. |
| 8,255,057 B2 | 8/2012 | Fang et al. |
| 8,335,569 B2 | 12/2012 | Aghassian |
| 8,335,664 B2 | 12/2012 | Eberle |
| 8,412,345 B2 | 4/2013 | Moffitt |
| 8,463,400 B2 | 6/2013 | Hegi et al. |
| 8,498,716 B2 | 7/2013 | Chen et al. |
| 8,594,797 B2 | 11/2013 | Lee |
| 8,606,362 B2 | 12/2013 | He et al. |
| 8,620,436 B2 | 12/2013 | Parramon et al. |
| 8,644,947 B2 | 2/2014 | Zhu et al. |
| 8,768,453 B2 | 7/2014 | Parramon et al. |
| 8,798,759 B2 | 8/2014 | Goetz et al. |
| 8,812,124 B2 | 8/2014 | Lee |
| 8,825,169 B2 | 9/2014 | Zhu et al. |
| 8,909,350 B2 | 12/2014 | Lee |
| 8,913,804 B2 | 12/2014 | Blum et al. |
| 9,014,820 B2 | 4/2015 | Lee et al. |
| 9,044,155 B2 | 6/2015 | Strahl |
| 9,061,140 B2 | 6/2015 | Shi et al. |
| 9,119,964 B2 | 9/2015 | Marnfeldt |
| 9,248,274 B2 | 2/2016 | Troosters et al. |
| 9,248,279 B2 | 2/2016 | Chen et al. |
| 9,259,574 B2 | 2/2016 | Aghassian et al. |
| 9,302,112 B2 | 4/2016 | Bornzin et al. |
| 9,387,334 B2 | 7/2016 | Lee et al. |
| 9,403,013 B2 | 8/2016 | Walker et al. |
| 9,409,020 B2 | 8/2016 | Parker |
| 9,526,897 B2 | 12/2016 | Chen et al. |
| 9,656,090 B2 | 5/2017 | Goetz |
| 9,731,116 B2 | 8/2017 | Chen |
| 10,076,667 B2 | 9/2018 | Kaula et al. |
| 2010/0305660 A1* | 12/2010 | Hegi .................. A61N 1/36071 607/60 |
| 2012/0095529 A1 | 4/2012 | Parramon et al. |
| 2012/0239109 A1* | 9/2012 | Lee .................... A61N 1/36185 607/45 |
| 2015/0012061 A1 | 1/2015 | Chen |
| 2015/0066111 A1* | 3/2015 | Blum ...................... A61B 6/12 607/59 |
| 2015/0080982 A1 | 3/2015 | Funderburk |
| 2015/0127062 A1 | 5/2015 | Holley |
| 2015/0231402 A1 | 8/2015 | Aghassian |
| 2015/0360038 A1 | 12/2015 | Zottola et al. |
| 2016/0144183 A1 | 5/2016 | Marnfeldt |
| 2016/0157769 A1 | 6/2016 | Min et al. |
| 2017/0189689 A1 | 7/2017 | Steinke et al. |
| 2017/0246449 A1 | 8/2017 | Goetz et al. |
| 2017/0281958 A1 | 10/2017 | Serrano Carmona et al. |
| 2017/0281959 A1 | 10/2017 | Serrano Carmona et al. |
| 2017/0296823 A1 | 10/2017 | Hershey et al. |
| 2018/0056078 A1 | 3/2018 | Kashyap et al. |
| 2018/0071513 A1 | 3/2018 | Weiss et al. |
| 2018/0071520 A1 | 3/2018 | Weerakoon et al. |
| 2018/0214701 A1 | 8/2018 | Zhang et al. |

OTHER PUBLICATIONS

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).

I. Akhoun et al., "Electrically evoked compound action potential artifact rejection by independent component analysis: Technique validation," Hearing Research 302, pp. 60-73 (2013).

M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).

H. Mino & J. Rubenstein, "Effects of Neural Refractoriness on Spatio-Temporal Variability in Spike Initiations with Eletrical Stimulation," IEEE Trans. on Neural Sys. & Rehabilitation Eng., vol. 14, No. 3, pp. 273-280 (2006).

M. Moffit et al., A Novel 3-Dimensional Algorithm for Model-Based Programming in Spinal Cord Stimuation (SCS): Illumina-3D™, presentation (2013).

J. Paz, "Physiological Midline Mapping Based on Spinal Cord Stimulation (SCS) Response Using the 32-Contact Paddle Lead," 19th NANS Annual Meeting (Dec. 13-15, 2015).

Precision Spectra™ System Programming Manual, Boston Scientific Corp., 90834018-18 Rev A (2016).

J. Rubinstein et al., "Pseudospontaneous activity: stochastic independence of auditory nerve fibers with electrical stimulation," Hear Res., 127(1-2), pp. 108-18 (1999) (abstract only).

J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).

A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

E. Viezi et al., "Spinal Cord Stimulation (SCS) with Anatomically Guided (3D) Neural Targeting Shows Superior Chronic Axial Low Back Pain Relief Compared to Traditional SCS—Lumina Study," Pain Medicine, pp. 1-15 (2017).

\* cited by examiner

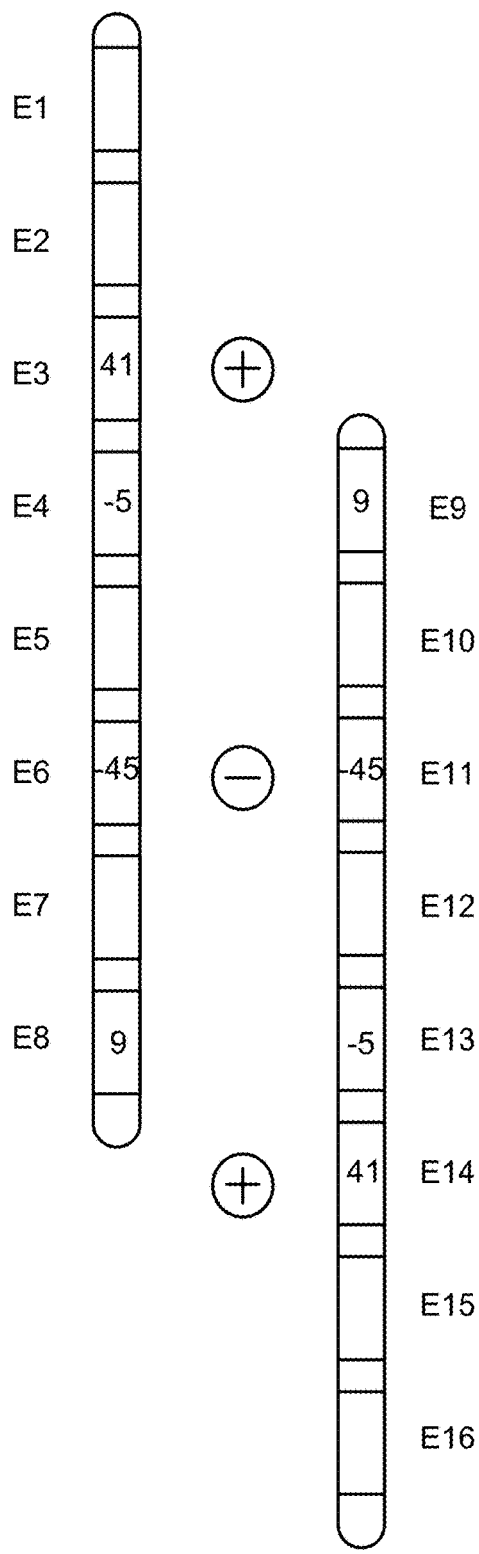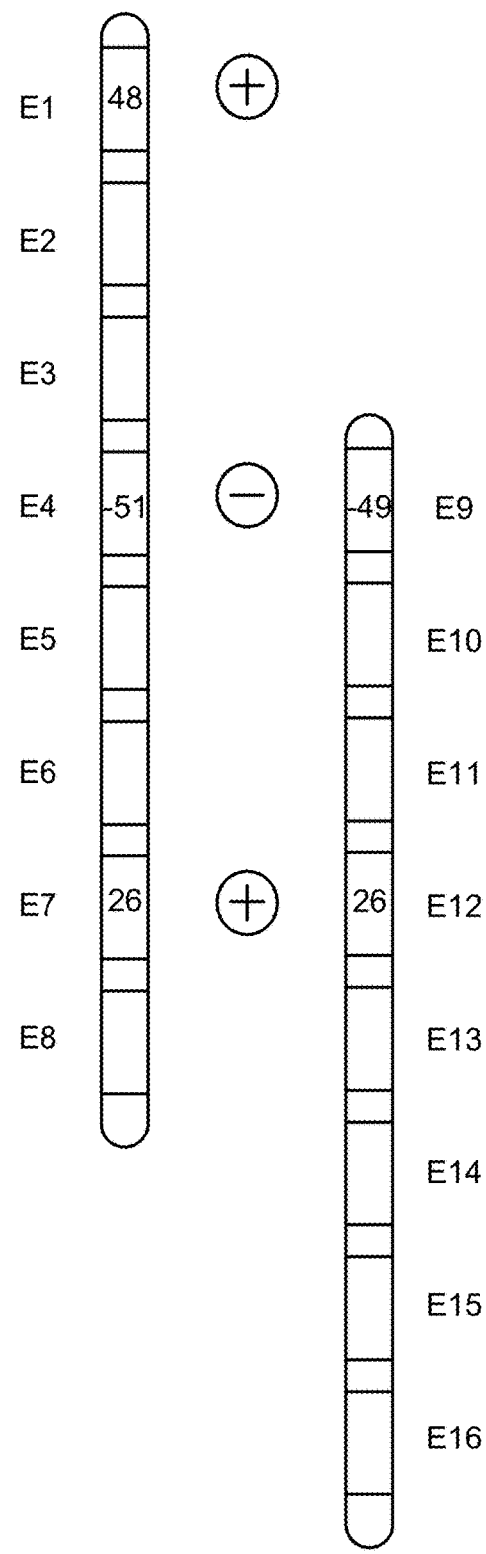
*Figure 8A*  *Figure 8B*

SYSTEM TO IMPROVE A SPINAL CORD STIMULATION MODEL BASED ON A PHYSIOLOGICAL MIDLINE LOCATION

CROSS REFERENCE TO RELATED APPLICATIONS

This is a non-provisional of U.S. Provisional Patent Application Ser. No. 62/583,332, filed Nov. 8, 2017, which is incorporated herein by reference in its entirety, and to which priority is claimed.

FIELD OF THE TECHNOLOGY

Implantable stimulation devices deliver electrical stimuli to nerves and tissues for the therapy of various biological disorders. The present application is related to a technique to improve the treatment of chronic pain using a Spinal Cord Stimulation (SCS) system. More specifically, the present application relates to techniques to identify the location of a spinal cord physiological midline, which location can be utilized to improve a spinal cord stimulation model.

INTRODUCTION

As shown in FIG. 1, a traditional SCS system includes an implantable neurostimulator such as an Implantable Pulse Generator (IPG) 10, which includes a biocompatible device case 12 formed of titanium, for example. The case 12 typically holds the circuitry and battery 14 (FIG. 2) necessary for the IPG 10 to function, which battery 14 may be either rechargeable or primary in nature. The IPG 10 delivers electrical stimulation to a patient's nerves and tissues through electrodes 16, which, in a SCS system are typically implantable within the epidural space within the spinal column. Common electrode arrangements include a linear arrangement along a percutaneous lead 18 and a two-dimensional arrangement on a paddle lead 60. The proximal ends of the leads 18 and 60 include lead connectors 20 that are connectabled to the IPG 10 at one or more connector blocks 22 fixed in a header 24, which can comprise an epoxy, for example. Contacts in the connector blocks 22 make contact with electrode terminals in the lead connectors 20, and communicate with the circuitry inside the case 12 via feedthrough pins 26 passing through a hermetic feedthrough 28 to allow such circuitry to provide stimulation to or monitor the various electrodes 16. The number and arrangement of electrodes on a percutaneous lead 18 or a paddle lead 60 can vary. When percutaneous leads 18 are employed, it is common for two such leads 18 to be implanted with one each on the right and left side of the spinal cord.

As shown in FIG. 2, IPG 10 contains a charging coil 30 for wireless charging of the IPG's battery 14 using an external charger 50, assuming that battery 14 is a rechargeable battery. If IPG 10 has a non-rechargeable (primary) battery 14, charging coil 30 in the IPG 10 and the external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include stimulation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external devices referenced above, which may be used to communicate with the IPG 10, in plan and cross section views. External controller (or, remote controller) 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify an electrode configuration that includes a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated, for example via Frequency Shift Keying (FSK) or the like, to encode transmitted data. For example, data telemetry via FSK can occur around a center frequency of fc=125 kHz, with a 129 kHz signal representing transmission of a logic '1' bit and a 121 kHz signal representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-holdable, portable housing.

External charger 50 provides power to recharge the IPG's battery 14 should that battery be rechargeable. Such power transfer occurs by energizing a charging coil 54 in the external charger 50, which produces a magnetic field comprising transcutaneous link 52, which may occur with a different frequency ($f_2$=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a single external system, such as disclosed in U.S. Pat. Nos. 8,335,569 and 8,498,716.

BRIEF DESCRIPTION OF THE DRAWINGS

FIGS. 7A-7C show the properties of different matrices that are used in the current mapping algorithm in accordance with an example of the disclosure.

FIGS. 8A and 8B show examples of the determined allocation of current among electrodes for different target stimulation fields in accordance with an example of the disclosure.

DETAILED DESCRIPTION

As mentioned above, the electrical stimulation that the IPG 10 is capable of delivering is highly customizable with respect to selected electrodes, electrode current amplitude and polarity, pulse duration, pulse frequency, etc. Due to uncertainties in the location of electrodes with respect to neural targets, the physiological response of a patient to stimulation patterns, and the nature of the electrical environment within which the electrodes are positioned, it is essentially impossible to determine the stimulation parameters that might provide effective stimulation therapy for a particular patient prior to implementing stimulation therapy. Thus, in order to determine whether the IPG 10 is capable of delivering effective therapy, and, if so, the stimulation parameters that define such effective therapy, the patient's response to different stimulation parameters is typically evaluated during a trial stimulation phase prior to the permanent implantation of the IPG 10.

During the trial stimulation phase, the distal ends of the lead(s) are implanted within the epidural space along the spinal cord while the proximal ends of the lead(s), including the electrode terminals 20, are ultimately coupled to an external neurostimulator such as external trial stimulator (ETS) 70, which is not implanted in the patient. The ETS 70 essentially mimics operation of the IPG 10 to provide stimulation to the implanted electrodes 16. This allows the effectiveness of stimulation therapy to be verified for the patient, such as whether therapy has alleviated the patient's symptoms (e.g., pain). Trial stimulation using the ETS 70 further allows for the determination of a particular stimulation program that seems promising for the patient to use once the IPG 10 is later implanted into the patient.

Figure 1:
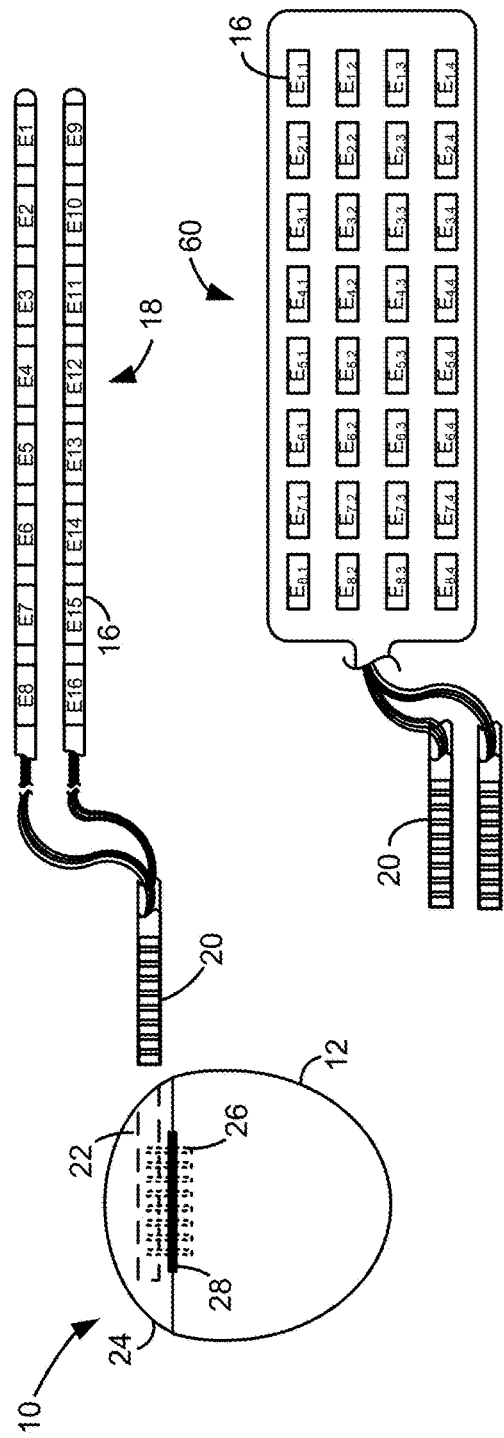
FIG. 1 shows an implantable pulse generator (IPG).
Figure 2:
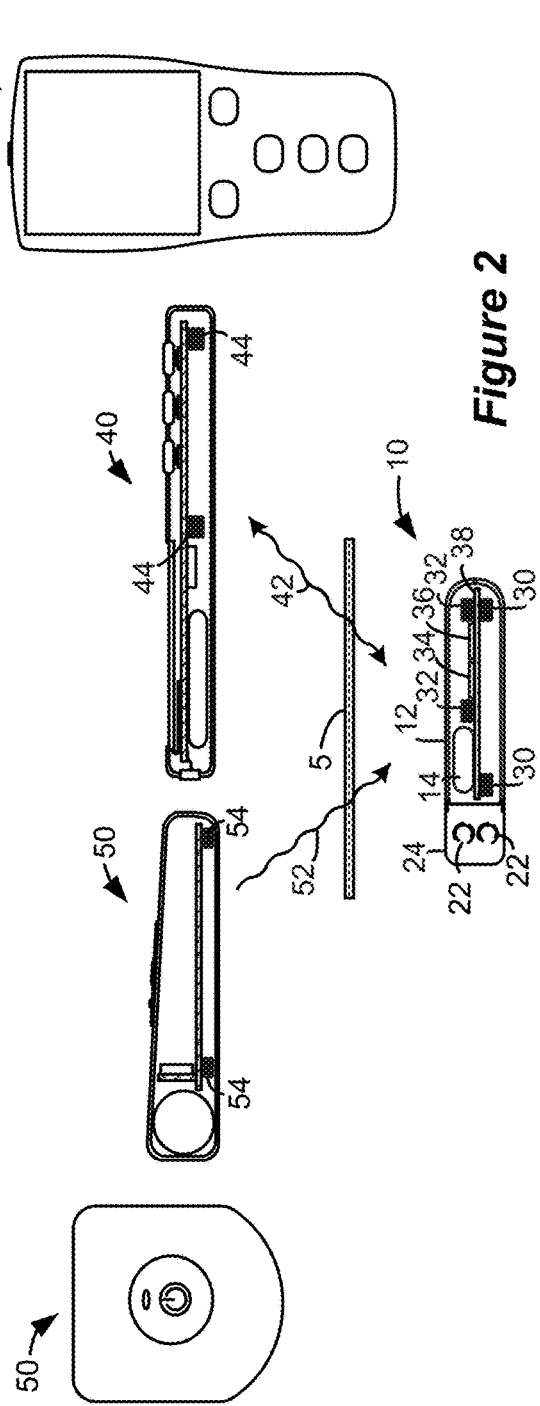
FIG. 2 shows a cross section of the IPG of FIG. 1 as implanted in a patient, as well as external devices that support the IPG, including an external charger and external controller.
Figure 3:
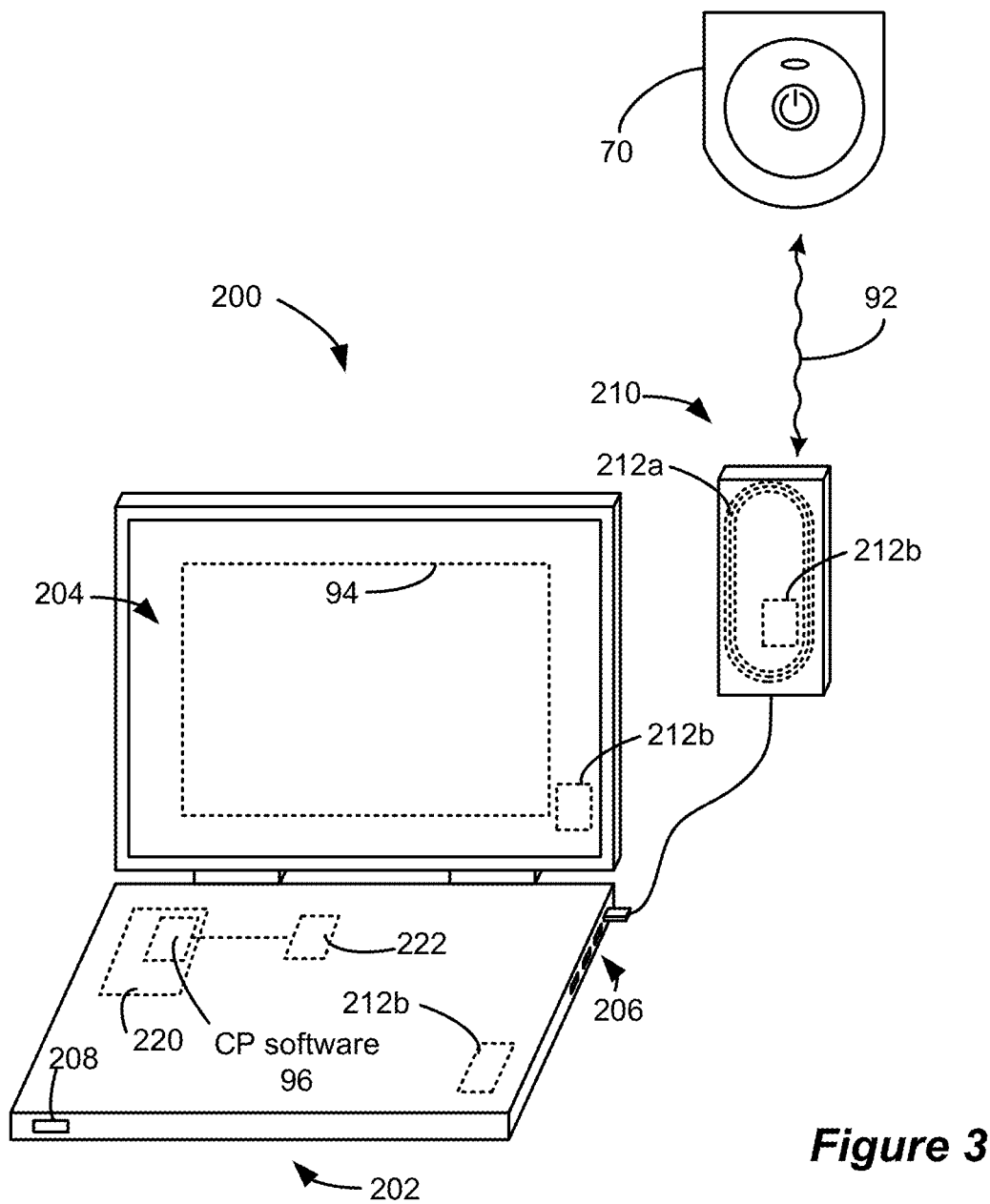
FIG. 3 shows components of a clinician's programmer system, including components for communicating with an external trial stimulator in accordance with an example of the disclosure.

Referring to FIG. 3, the stimulation program executed by the ETS 70 can be provided or adjusted via a wired or wireless link (wireless link 92 shown) from an additional external device known as a clinician's programmer 200, which includes features (described below) that enable a clinician to hone in on the appropriate stimulation therapy settings. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 3, CP computer 202 is shown as a laptop computer that includes typical computer user interface means such as a screen 204, a mouse, a keyboard, speakers, a stylus, a printer, etc., not all of which are shown for convenience. Also shown in FIG. 3 is a communication head 210, which is coupleable to a suitable port on the CP computer 202, such as a USB port 206, for example. While the CP system is shown in communication with the ETS 70, the CP system 200 is also configured to communicate with the IPG 10 once it is implanted.

Communication between the CP system 200 and the ETS 70 or IPG 10 may comprise magnetic inductive or short-range RF telemetry schemes as already described, and in this regard the ETS 70 and the CP computer 202 and/or the communication head 210 (which can be placed proximate to the IPG 10 or ETS 70) may include antennas compliant with the telemetry means chosen. For example, the communication head 210 can include a coil antenna 212$a$, a short-range RF antenna 212$b$, or both. The CP computer 202 may also communicate directly with the IPG 10 of the ETS 70, for example using an integral short-range RF antenna 212$b$.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To program stimulation parameters, the clinician interfaces with a clinician's programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer's non-volatile memory 220. Such non-volatile memory 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 enable communications with the ETS 70 through a suitable antenna 212a or 212b, either in the communication head 210 or the CP computer 202 as explained earlier, so that the clinician can use the CP GUI 94 to communicate the stimulation parameters to the ETS 70.

Figure 4:
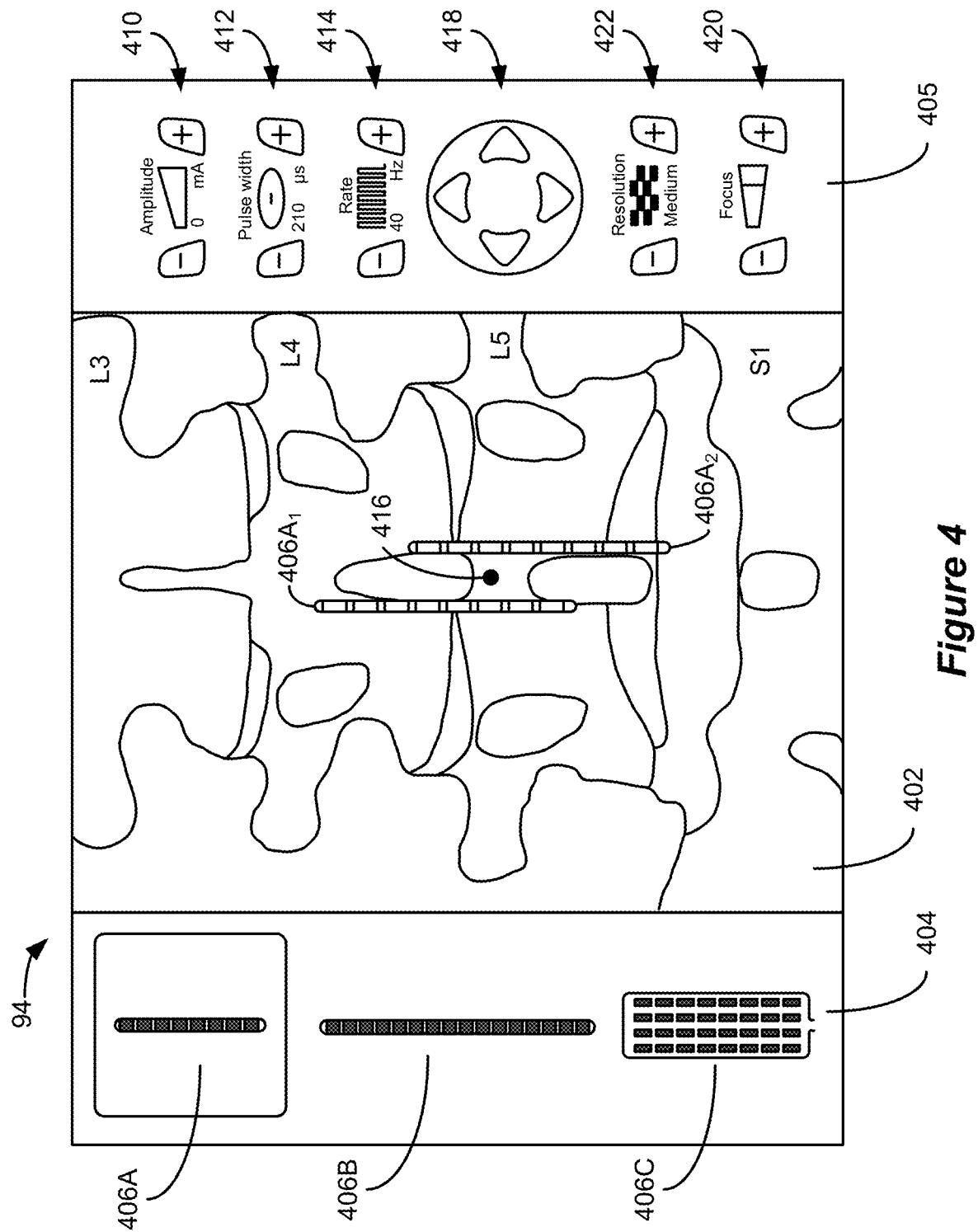
FIG. 4 shows an example of a graphical user interface that can be provided on the clinician's programmer system in accordance with an example of the disclosure.

An example of a portion of the CP GUI 94 is shown in FIG. 4. The illustrated portion of the GUI 94 includes fluoroscopic image 402, which shows the implanted leads relative to anatomical structures, such as vertebrae. Using the illustrated interface, a user can select a representation 406 of the implanted electrode lead from left side panel 404, which includes representations 406 of various types of lead products such as 1×8 percutaneous lead representation 406A, 1×16 percutaneous lead representation 406B, and 4×8 paddle lead representation 406C. The user can then drag the selected lead representation 406 onto the fluoroscopic image 402 and manipulate its size and orientation until it aligns with the implanted electrode lead in the image 402. Because the representations 406 are programmed with properties of the lead such as electrode size, shape, and spacing, the positioning of a lead representation 406 on the fluoroscopic image 402 relates the locations of the electrodes to the image 402. This enables a user to subsequently visualize through the GUI 94 the anatomical location of electrical stimulation as described below.

Such anatomical visualization of electrical stimulation can be beneficial in determining the desired stimulation program due to the spatial relationship between the point of stimulation and the location at which the effect of stimulation is perceived by a patient. While the precise mechanism by which spinal cord stimulation interrupts the sensation of pain is not fully understood, it is understood that the stimulation of a spinal nerve on a particular side of a patient's body results in the perception of stimulation (or simply the interruption of what was previously perceived as pain) on the same side of the body. For example, pain in the upper right leg, which is perceived as a result of the transmission of a neurological signal through sensory neurons from the location of the pain through a spinal nerve on the same side of the body and into the spinal cord where it is further transmitted to the brain, is interrupted by the application of electrical stimulation to the spinal nerve through which the pain signal travels (i.e., the spinal nerve on the right side of the body). Therefore, the visualization of the anatomical point of stimulation provides information that can guide the user in determining the appropriate stimulation parameters to treat a patient's particular pain symptoms.

Various inputs regarding the location and properties of stimulation can be provided by the user through interactive elements in the right side panel 405 of the GUI 94 as further illustrated in FIG. 4. The stimulation amplitude, pulse width, and frequency can be adjusted using the buttons 410, 412, and 414, respectively. The center point 416 of the desired stimulation field can be moved horizontally and vertically using the arrows 418. The shape of the target stimulation field can be customized, but, in one example, the target stimulation field may be represented by a tripole consisting of a target cathode at the center point of stimulation and two target anodes at equal distances from the cathode along a line that is parallel with the anatomical midline (i.e. along a vertical line in the interface 94). The focus of the target stimulation field, which is the distance between the target cathode and each target anode, can be adjusted using the focus buttons 420. The magnitude of the adjustments that are effected via the arrows 418 and the focus buttons 420 can be set at different granularity levels (e.g., coarse, medium, and fine) via the resolution buttons 422.

Figure 5:
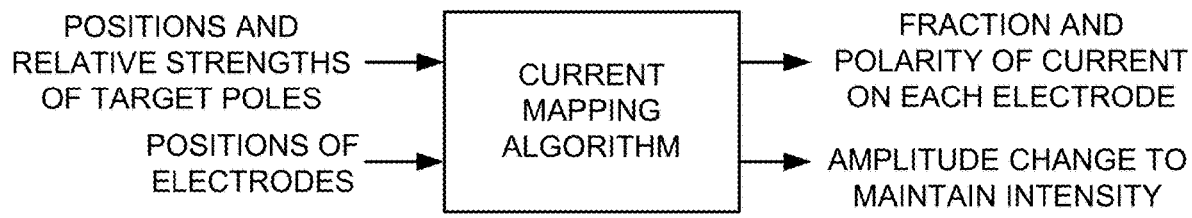
FIG. 5 is a block diagram that shows the inputs to and the outputs from a current mapping algorithm that can be used to determine the parameters of spinal cord stimulation in accordance with an example of the disclosure.

While the target stimulation field could be generated by providing stimulation at the locations of the target poles (i.e., the target cathode and target anodes), the target poles do not necessarily correspond to the location of physical electrodes. Thus, a current mapping algorithm, which is part of the CP software 96, is employed to compute the fraction of the total stimulation current that should be sourced to or sunk from each physical electrode to best represent the electric field that would result from stimulation at the target poles. As illustrated in FIG. 5, the inputs to the current mapping algorithm are the positions and relative strengths of the target poles and the positions of the physical electrodes. From these inputs, the current mapping algorithm outputs the current fraction and polarity of current that should be delivered to each physical electrode to mimic the target stimulation field as well as an amplitude change that is necessary to maintain stimulation intensity as is now briefly explained. These properties form part of the electrode configuration that is communicated to the neurostimulator.

The current mapping algorithm includes a model (such as a finite element model) that can be used to evaluate properties of the electric field that would be generated as a result of stimulation at the target poles. As used herein, modeling an electric field or generating a model of an electric field refers to determining one or more electrical properties at different spatial locations. Similarly, an electric field model refers to the values of the one or more electrical properties at the different spatial locations. The electrical properties may include the magnitude and/or direction of the electric field itself, the magnitude of an electric potential, the magnitude of a current, or other electrical properties at the different spatial locations. Thus, an electric field model does not necessarily refer to values of the strength and direction of an electric field (as the model may include a collection of other electrical values such as electric potentials) and does not imply that values exist at every spatial location within a volume of tissue but rather at a determined number of locations.

Figure 6:
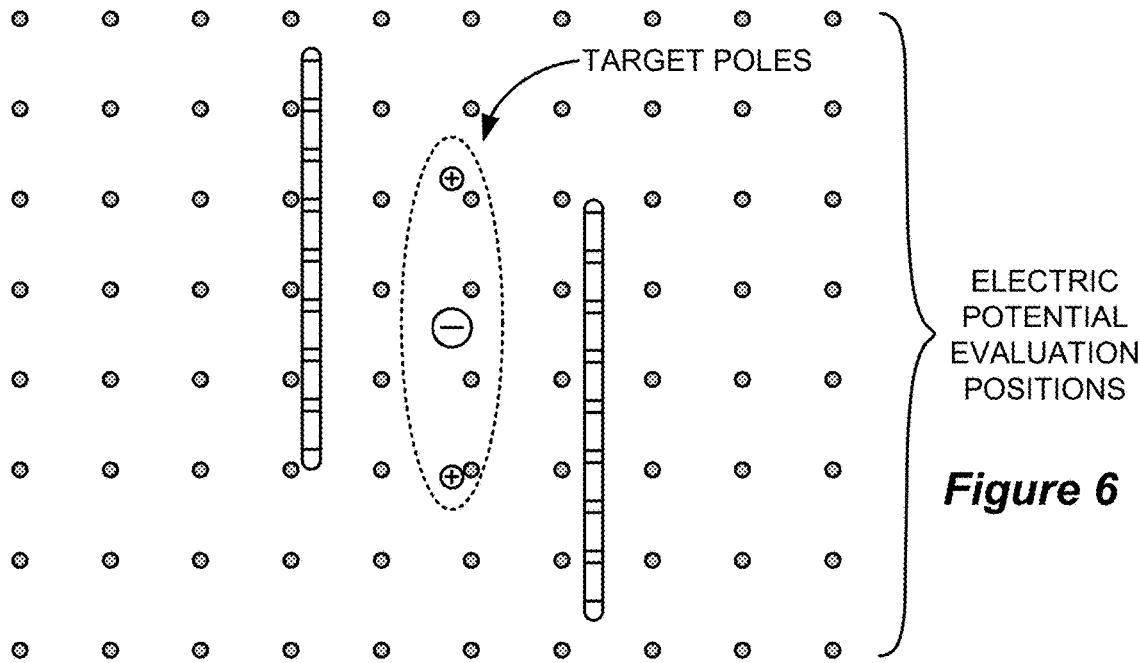
FIG. 6 shows a portion of the current mapping algorithm that is used to determine the fraction and polarity of electrodes that best matches a target stimulation field in accordance with an example of the disclosure.

In an example, the model takes into account the electrical properties of different anatomical structures such as white matter, gray matter, cerebral spinal fluid, epidural space, dura, and vertebral bone in the area of the target poles to determine the electric potential that would be induced at each of m electric potential evaluation positions as a result of stimulation at the target poles. The electric potential evaluation positions may be arranged in a grid as shown in FIG. 6. While a small number of evaluation positions are shown for purposes of illustration, in an actual implementation the spatial resolution of the evaluation positions may be much higher. The modeled electric potentials at the m evaluation positions that would result from stimulation at the target poles form a m×1 vector, φ (FIG. 7A).

The model is also used to determine the electric potentials that would be induced at the m evaluation positions as a result of stimulation via n physical electrode arrangements. While the modeled electrode arrangements can include any combination of electrodes (e.g. bipoles, tripoles, etc.), in one example, the n electrode arrangements are each bipole arrangements (e.g., E1 is 100% cathode and E2 is 100% anode, E2 is 100% cathode and E3 is 100% anode, etc.). The electric potentials at the m evaluation positions that are determined as a result of modeling stimulation via the n electrode arrangements form a m×n transfer matrix, A (FIG. 7B). Any number of electrode arrangements can be modeled to increase the size of the transfer matrix A, and the solution accuracy and computational difficulty are both increased as the number of electrode arrangements n is increased.

The electric potentials that would be formed at the m evaluation positions as a result of a combination of various electrode arrangements can be determined by multiplying the transfer matrix A with a n×1 vector j (FIG. 7C) that specifies the proportions (X) of each of the n electrode arrangements. The combination of electrode arrangements that would induce electric potentials at the m evaluation positions that best match those generated as a result of stimulation at the target poles can be determined by solving for the value of j that minimizes the equation $|\varphi-Aj|^2$. The relative proportions of the electrode arrangements in the calculated value of j can be converted to the electrode current fractions and polarities that would result in an electric potential field that most closely mimics the target stimulation field.

The current fractions and polarities that may be computed by the current mapping algorithm for example target stimulation fields are illustrated in FIGS. 8A and 8B. In the figures, two percutaneous leads are shown. The leads are offset by three electrodes with the left lead inserted further than the right lead. In FIG. 8A, the target stimulation field is represented by a tripole having a center point of stimulation that is positioned between electrodes E6 and E11 and a focus of three times the electrode-to-electrode spacing on the leads. The output of the current mapping algorithm specifies that the target stimulation field is best represented when 41% of the anodic current is allocated to each of electrodes E3 and E14, 9% of the anodic current is allocated to each of electrodes E8 and E9, 45% of the cathodic current is allocated to each of electrodes E6 and E11, and 5% of the cathodic current is allocated to each of electrodes E4 and E13. In FIG. 8B, the target stimulation field is represented by the same tripole as in FIG. 8A except the center point of stimulation is shifted such that it is positioned between electrodes E4 and E9. The output of the current mapping algorithm specifies that this target stimulation field is best represented when 51% of the anodic current is allocated to electrode E4, 49% of the anodic current is allocated to electrode E9, 26% of the cathodic current is allocated to each of electrodes E7 and E12, and 48% of the cathodic current is allocated to electrode E1. The determination of current fractions and polarities that best match a target stimulation field is described in greater detail in U.S. Pat. No. 8,412,345, which is incorporated herein by reference in its entirety.

In addition to determining the fraction and polarity of current that should be delivered to each electrode to best represent the target stimulation field, the current mapping algorithm additionally determines whether and to what extent the total stimulation amplitude should be adjusted to maintain constant stimulation intensity. The determined allocation of current between the electrodes is input to the model described above to determine the resulting spatial distribution of electric potentials for a baseline stimulation amplitude (e.g., total stimulation amplitude of 1 mA). The modeled potentials are assumed to scale linearly with increasing stimulation amplitude and are adjusted from the baseline amplitude to the actual stimulation amplitude that is being used.

Figure 9:
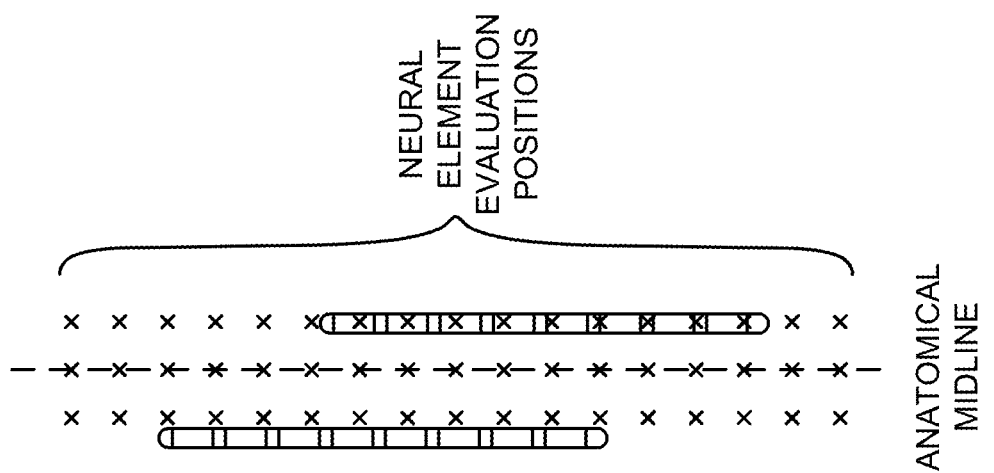
FIG. 9 shows a portion of the current mapping algorithm that is used to maintain an intensity of stimulation in accordance with an example of the disclosure.

The current mapping algorithm then employs a neural element model to evaluate the response of neural elements to the electric field. The neural element model incorporates morphological and electrical properties to evaluate the response of neural elements to the different electric field properties that are observed at different neural element evaluation positions. For example, the neural element model may compute, based on the electric field properties, the transmembrane potentials that are induced at the Nodes of Ranvier of the dorsal column fibers. The evaluation positions are located along the assumed path of the dorsal column fibers along the anatomical midline as shown in FIG. 9. Note that the neural element evaluation positions are different from the electric potential evaluation positions shown in FIG. 6. Based on the modeled electric potentials as well as other stimulation parameters such as frequency and pulse width, the neural element model can be utilized to determine whether the neural elements at each evaluation position would be activated by the stimulation. Note that while the neural element evaluation positions are symmetrical with respect to the anatomical midline, they are not necessarily symmetrical with respect to the electrode leads and thus the allocation of current to different electrodes may result in the different activations of neural elements at different ones of the evaluation positions. For example, in FIG. 9, the right lead is positioned nearer to the assumed location of the dorsal column fibers (and therefore nearer to the evaluation positions), so stimulation using electrodes on the right lead would be expected to activate a larger number of dorsal column neural elements. Therefore, as the center point of stimulation is moved from left to right, the same stimulation amplitude would result in the activation of increasing numbers of neural elements. To maintain the same stimulation intensity as the location of stimulation is moved, the total stimulation amplitude is adjusted to keep the volume of activation (i.e., the number of neural elements that are determined to be activated by a particular electric field) relatively constant. U.S. Pat. No. 8,644,947, which is incorporated herein by reference in its entirety, describes in greater detail the adjustment of stimulation amplitude to maintain stimulation intensity.

As described above, the current mapping algorithm relies upon the assumption that the dorsal column fibers are aligned with the patient's anatomical midline (i.e., vertical in the GUI 94). Specifically, the current mapping algorithm uses this assumption to place the anodes along a line that intersects the selected center point of stimulation and that is parallel with the vertical anatomical midline and further assumes that the neural element evaluation positions extend along lines that are parallel with the anatomical midline. The inventors have determined that these assumptions are not necessarily accurate and that the current mapping algorithm can be improved by constructing the desired stimulation field and evaluating the effect of stimulation at neural evaluation positions based on the location of the physiological midline.

Figure 10:
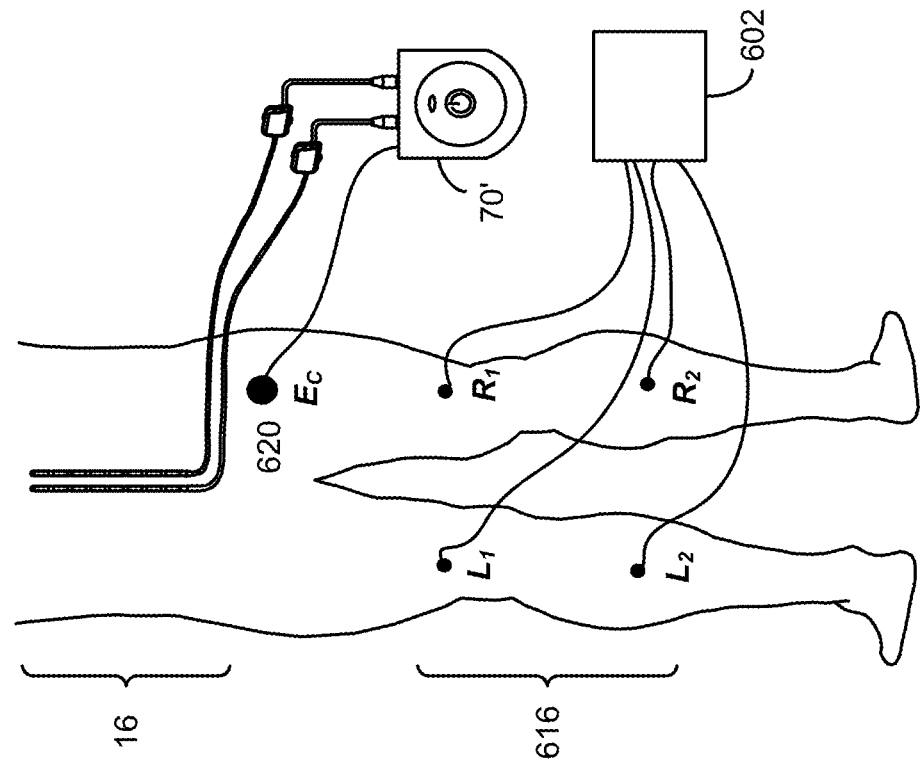
FIG. 10 shows the connection of spinal and peripheral electrodes to an external trial stimulator and a monitoring electrode device for determining the location of a physiological midline in accordance with an example of the disclosure.

The location of the physiological midline can be determined by evaluating the patient's response to stimulation. Such response can be derived from measurements associated with one or more of the implanted electrodes 16 as is now described. Referring to FIG. 10, in one example, peripheral electrodes 616 (labeled $L_1$, $L_2$, $R_1$, and $R_2$) are utilized in conjunction with spinal electrodes 16 on one or more implanted electrode leads (such as leads 18 or 60) to determine the location of the physiological midline based on the peripheral response to spinal stimulation at different electrodes 16. As used herein, a peripheral electrode is an electrode positioned at a location of a patient other than the patient's spinal column that can measure an electrical response to stimulation of a spinal electrode or induce a response (via electrical stimulation of the peripheral electrode) that is observable at a spinal electrode. Four electromyography (EMG) peripheral electrodes 616 are shown in FIG. 10, but more or fewer electrodes may also be employed. While EMG peripheral electrodes 616 are described, different types of biosignals that can be evaluated at known lateral positions (i.e., right or left) can also be employed. Moreover, while EMG electrodes are depicted as being placed in or on different leg muscles, the peripheral monitoring electrodes may be placed at any peripheral muscle locations having a known lateral position.

The disclosed technique operates on the principle that spinal cord stimulation on a particular side of a physiological midline results in the recruitment of a greater number of neurons on the same side of the physiological midline than on the opposite side of the physiological midline. This imbalance is detectable as a difference in electrical activity at corresponding peripheral monitoring electrodes on different sides of the body. For example, in the case of EMG peripheral electrodes, spinal cord stimulation on the right side of the physiological midline results in the recruitment of a greater number of motor neurons on the right side of the physiological midline than on the left side of the physiological midline, which results in muscle activity (e.g., contractions) that is more pronounced on the right side, which is detectable as an EMG signal having a greater amplitude on the right side.

Because the technique is based upon relative responses on different sides of the body, the monitoring electrodes are preferably arranged in corresponding pairs. For example, if electrode $L_1$ is placed over or in the lower left quadriceps muscle, electrode $R_1$ is preferably placed over or in the lower right quadriceps muscle. Similarly, if electrode $L_2$ is placed over or in the middle of the left gastrocnemius muscle, electrode $R_2$ is preferably placed over or in the middle of the right gastrocnemius muscle.

The peripheral electrodes 616 are coupled to circuitry within a monitoring electrode device 602 and the spinal electrodes 16 (i.e., the electrodes on the implanted lead(s)) are stimulated by circuitry within a modified ETS 70', which is modified in the sense that it is additionally configured to stimulate a complementary electrode ($E_C$) 620, the function of which will be described below. Although a modified ETS 70' is shown, the spinal electrodes 16 and the complementary electrode 620 may alternatively be stimulated by a dedicated stimulating device.

Figure 11:
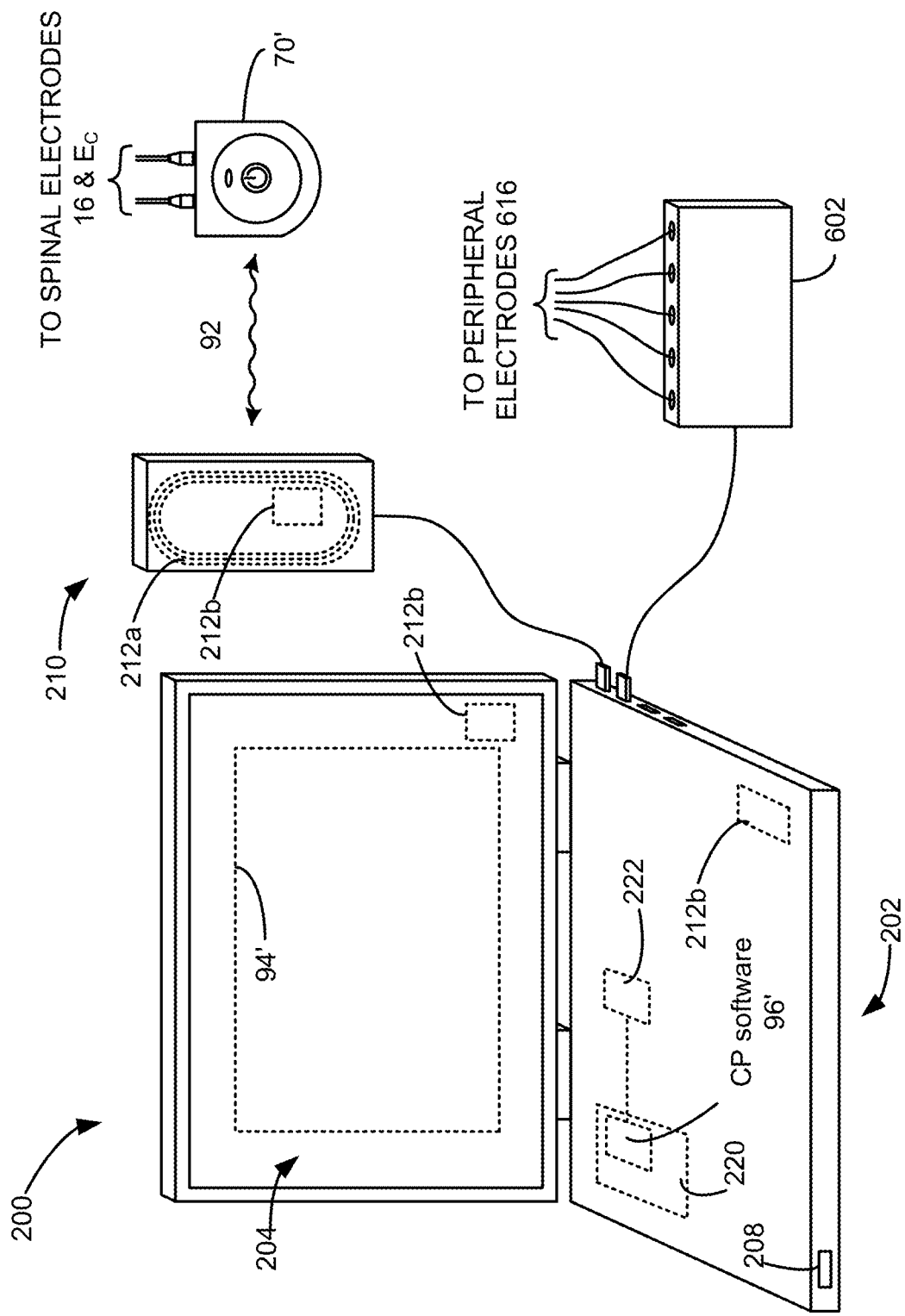
FIG. 11 shows the connection of the external trial stimulator and the monitoring electrode device to a clinician's programmer system in accordance with an example of the disclosure.

As illustrated in FIG. 11, the modified ETS 70' and the monitoring electrode device 602 are connected to the CP computer 202. While different wired and wireless connections are shown, the monitoring electrode device 602 and the modified ETS 70' (or the separate dedicated stimulating device) can be connected to the CP computer 202 in any way that allows the relevant commands and data to be passed between the devices. The CP computer 202 executes improved CP software 96', which incorporates physiological midline determination algorithms, as described below, an improved GUI 94', and an improved current mapping algorithm, which utilizes the determined location of the physiological midline as described below.

The CP computer 202 includes control circuitry 222 (such as a microcontroller) that communicates with the modified ETS 70' and the monitoring electrode device 602. In particular, the CP computer 202 sends stimulation instructions to the modified ETS 70' and receives data from the monitoring electrode device 602, which instructions and data may be provided and received in accordance with the execution of a physiological midline algorithm by the control circuitry 222.

The modified ETS 70' includes control circuitry, which may comprise a microcontroller, that receives the stimulation instructions from the CP computer 202 and communicates the instructions to one or more Digital-to-Analog converters (DACs), which are used to produce currents or voltages of prescribed amplitudes (A) for the stimulation pulses, and with the correct timing. The peripheral electrodes 616 are each coupled to circuitry within the monitoring electrode device 602 that can select and digitize the signals from the various peripheral electrodes 616. The monitoring electrode device 602 may additionally include a memory for storing the digitized signals. Because the algorithm must be aware of the lateral position associated with signals it receives from the peripheral electrodes 616, the monitoring electrode device 602 may have ports that are marked to indicate the position of the signal that should be routed to that port (i.e., left or right) or the algorithm may enable a user to specify the lateral position associated with the signals routed to different ones of the device 602's ports.

The algorithm operates to determine the location of the physiological midline by stimulating various spinal electrodes 16 and observing the response at peripheral electrodes 616 at different lateral positions. Initially, a first spinal electrode 16 is stimulated at a starting amplitude level (e.g., 5 mA). The selected spinal electrode 16 is preferably stimulated in combination with the complementary electrode 620. Specifically, the complementary electrode 620 is stimulated at an equal magnitude and an opposite polarity from the selected spinal electrode 616. The complementary electrode 620 is preferably a surface electrode (i.e., adhered to the patient's skin) having a relatively large area and is positioned remotely from the spinal electrodes 16 as well as from the peripheral electrodes 616. The remote location and the large area of the complementary electrode 620 ensures that its stimulation does not interfere with the signals measured at the peripheral electrodes 616 and that the spinal electrode 16 (which produces a localized field in close proximity to a spinal nerve), and not the complementary electrode 620, is responsible for any observed reaction at the peripheral electrodes 616. Although the use of complementary electrode 620 is described, stimulation may also occur using two or more spinal electrodes 16 that are in close proximity to one another (e.g., neighboring electrodes may serve as an anode and cathode). In fact, as described below, simultaneous stimulation of multiple spinal electrodes 16 can enable greater spatial resolution through the creation of "virtual" electrodes and can additionally enable use of a conventional ETS 70 (i.e., without modification to accommodate the complementary electrode 620). In one embodiment, the selected electrode and the complementary electrode 620 are stimulated using a square waveform having a low frequency of approximately 2-10 Hz. However, the desired stimulation waveform and amplitude may be user-selectable parameters.

During stimulation, the signals from each of the peripheral electrodes 616 are recorded either serially (e.g., via a multiplexer) or in parallel if dedicated circuitry is provided for each electrode. Such recording may involve the storage in memory (either in CP system 200 or monitoring electrode device 602) of the digitized values of the signals. The stimulation amplitude is increased sequentially until a bilateral response (i.e., a detectable response at corresponding peripheral electrodes on different sides of the body) is recorded or until some other safety cutoff (e.g., maximum stimulation amplitude or maximum amplitude increase after unilateral response is observed) is reached. The process is then repeated for each of the remaining spinal electrodes 16 that are to be evaluated.

The responses that are recorded at the peripheral electrodes 616 as a result of stimulation for each of the spinal electrodes 16 are quantified through any of a variety of metrics such as the root mean square (RMS) of sampled values, the integral of rectified sampled values during a time period (e.g., all or part of a stimulation time period), or other known statistical measures. From the quantified values, a measure of the spinal electrode 16's position with respect to the physiological midline can be computed. The measure of each spinal electrode 16's position can be expressed as a ratio based on the lateral responses of the peripheral electrodes 616 during execution of the algorithm. For example, the ratio can be calculated as the sum of the quantified responses at the peripheral electrodes 616 on the left side of the patient's body over the sum of the quantified responses at the peripheral electrodes 616 on the right side of the patient's body. The quantified responses that are included in such a ratio can be selected in different ways. Such a ratio quantifies the degree to which a spinal electrode is left or right of the physiological midline. For example, if the ratio is expressed as a left/right ratio, a value of one indicates alignment with the physiological midline, a value of greater than one indicates a position (and the relative distance) left of the physiological midline, and a value of less than one indicates a position (and the relative distance) right of the physiological midline. While a left/right ratio is described, there are other ways in which the position and relative distance from the physiological midline may be expressed based on the responses measured at the peripheral electrodes.

Figure 12:
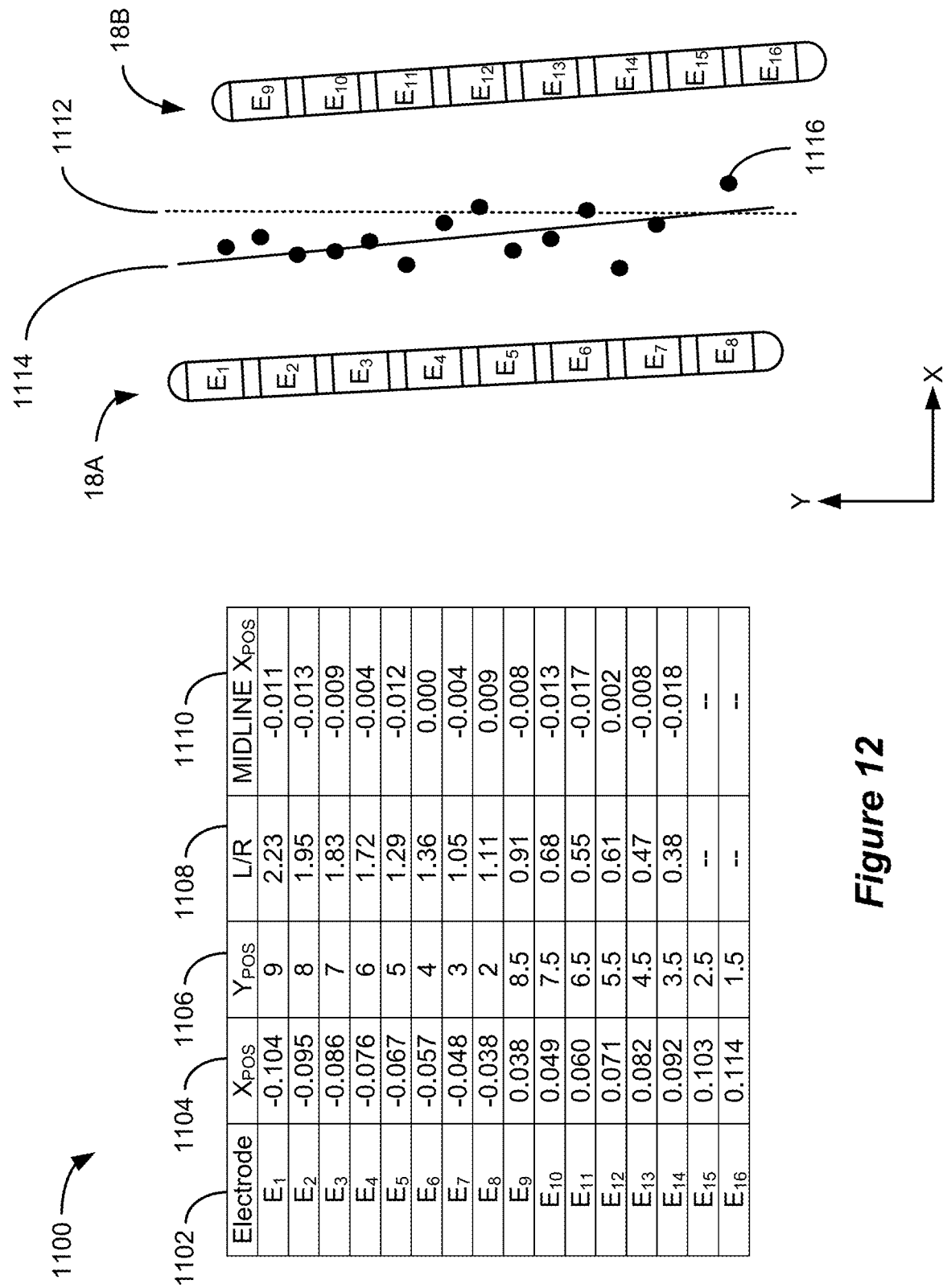
FIG. 12 shows an example data set and its use in determining the location of a physiological midline in accordance with an example of the disclosure.

FIG. 12 illustrates an example data set 1100 associated with execution of the physiological midline algorithm. The data set 1100 includes an electrode identifier 1102, horizontal and vertical electrode positions 1104 and 1106, the measure of the electrode's position with respect to the physiological midline (expressed as response ratio 1108), and a midline horizontal position 1110. The horizontal and vertical positions of the electrodes 1104 and 1106 are determined, for example, based on the placement of a lead representation 406 over a fluoroscopic image 402 (FIG. 4), which establishes a spatial relationship of the spinal electrodes 16 that matches their actual positions. The coordinate system in the illustrated example employs a horizontal value of zero along an anatomical midline 1112, but the selection of a coordinate system is arbitrary. As shown, both electrode leads 18A and 18B have a slight slope with respect to the anatomical midline 1112.

The horizontal position of the physiological midline 1110 is calculated based on the response ratio 1108 and the known horizontal position of the corresponding spinal electrode 16. The first step in determining the horizontal midline position 1110 is relating the response ratio 1108 to a distance from the physiological midline. For example, $E_1$'s left/right ratio value of 2.23 indicates that it is the furthest left of the physiological midline of any electrode. However, this value must still be related to a distance from the physiological midline. In the illustrated embodiment, an electrode's left/right ratio value 1108 is multiplied by an initial correlation value, which is a predetermined value that approximates the relationship between the response ratio 1108 and the distance in the adopted coordinate system, and the resulting value is added to (or subtracted from if electrode is right of midline) the electrode's horizontal position value 1104. The calculated horizontal position of the physiological midline 1110 is utilized in conjunction with the electrode's vertical position as the electrode's contribution to the midline location. For example, electrode $E_1$'s left/right ratio value of 2.23 is multiplied by a correlation value of 0.042 to obtain a distance to midline value of 0.093, which is added to $E_1$'s horizontal position value of −0.104 to obtain the midline horizontal position of −0.011. The horizontal position of the physiological midline 1110 is utilized in conjunction with $E_1$'s vertical position of 9 to determine $E_1$'s contribution to the midline calculation—a point having a vertical position of 9 and a horizontal position of −0.011. The same calculation is repeated for each of the spinal electrodes 16 and the location of the physiological midline is determined based on the set of points 1116. For example, a linear regression may be performed using the set of points 1116 to determine the equation of the physiological midline 1114 in the adopted coordinate system.

It will be understood that if the correlation value is not accurate, the resulting determination of the physiological midline 1114 may be flawed. For example, if the correlation value is too large, the calculated horizontal values will "overshoot" the physiological midline 1114. For example, electrodes left of the midline 1114 will contribute a data point that is right of the midline 1114 and vice versa. Likewise, if the correlation value is too small, the calculated horizontal values will "undershoot" the physiological midline 1114. In order to determine the ideal correlation value, the physiological midline location is calculated through an iterative process. This may be accomplished by evaluating the "fit" of the computed physiological midline 1114 to the set of points 1116, adjusting the correlation value (in a direction dictated by whether there is an "overshoot" or "undershoot" error), and repeating the process. The process can be iteratively repeated until the equation of the physiological midline best "fits" the points 1116. This can be accomplished, for example, by identifying the correlation value that maximizes the coefficient of determination (i.e., the R squared value). Note that the points shown in FIG. 12 are based on a correlation value that is near the ideal value.

While the physiological midline algorithm has been described in the context of stimulation between a single selected spinal electrode 16 and the corresponding electrode 620, "virtual" electrodes can also be created through the stimulation of combinations of spinal electrodes 16. The use of such virtual electrodes can provide additional stimulation locations that can be considered as part of the data set 1100, which can improve the results. Such virtual electrodes may be considered to be located in the position that represents the centroid of spinal stimulation. The physiological midline algorithm can be slightly modified for paddle leads such as lead 60 to increase efficiency. More specifically, the algorithm can be modified such that the midline location (e.g., the location with a response ratio closest to unity) is determined for a particular row of electrodes 16 (perhaps using virtual electrodes constructed from a combination of electrodes in the row) before moving vertically to the next row of electrodes.

Figure 13:
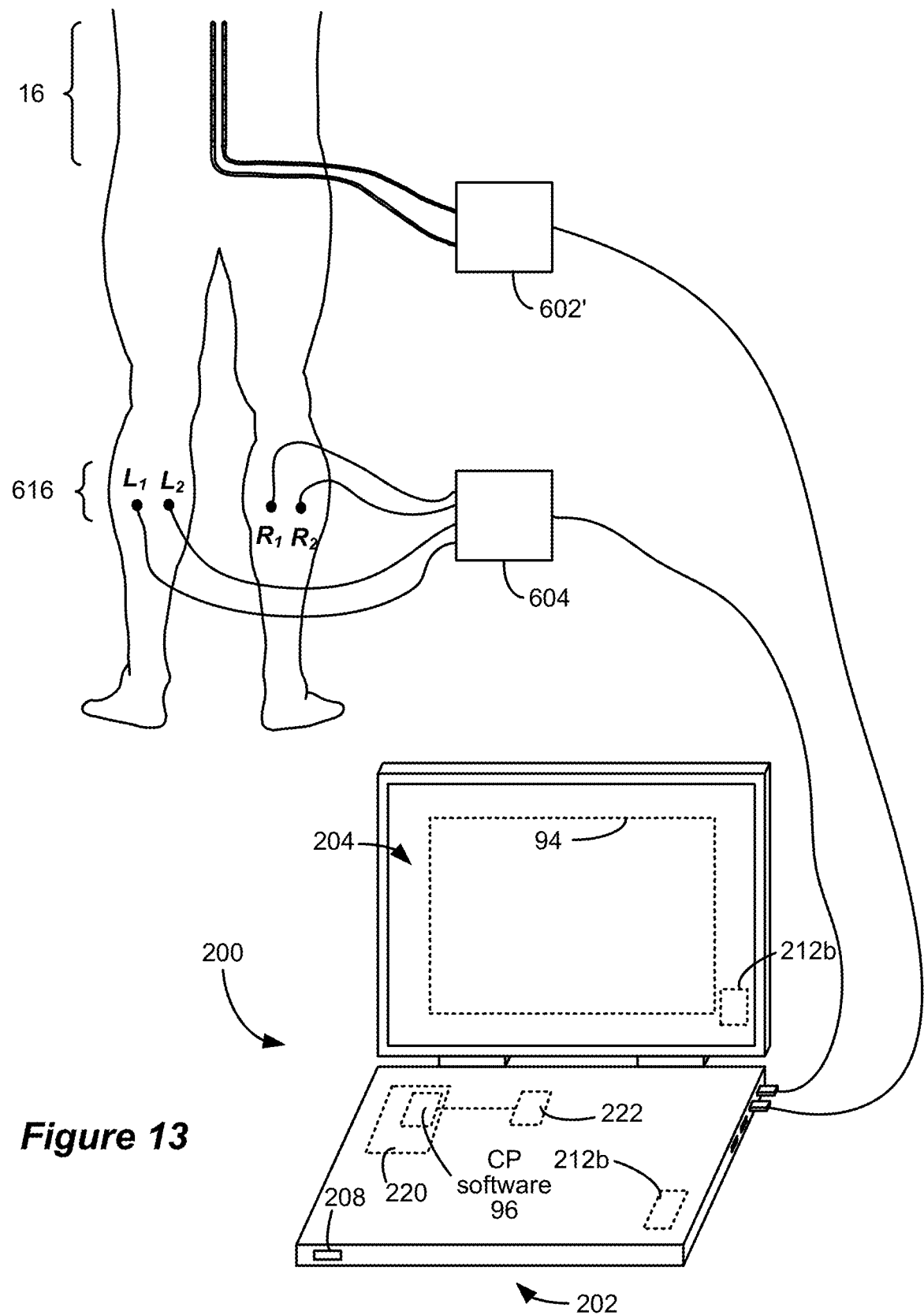
FIG. 13 shows the connection of a stimulating electrode device and a monitoring electrode device to a clinician's programmer system in accordance with an example of the disclosure.

In an alternative method, peripheral electrodes 616 can be employed as stimulating electrodes and spinal electrodes 16 as monitoring electrodes to determine the location of the physiological midline. In FIG. 13, the spinal electrode leads (two percutaneous leads 18 are shown) are electrically coupled to circuitry within a modified monitoring electrode device 602', which is modified from the device 602 in the sense that it may include a connector block similar to the connector block 22 to couple the individual electrodes 16 to the monitoring circuitry, and the peripheral electrodes 616 are connected to circuitry within a stimulating electrode device 604. The devices 602' and 604 are connected to the CP computer 202's USB ports 206; however, other wired or wireless connections can be employed as noted above. Because stimulation of a corresponding electrode ($E_C$) such as that utilized in the peripheral monitoring embodiment invokes the same type of response as stimulation at the peripheral electrodes 616, it is not utilized in the spinal monitoring embodiment. Instead, stimulation occurs between a pair of peripheral electrodes 616 located on the same side of the body, such as $L_1$ and $L_2$ or $R_1$ and $R_2$. While the pairs of peripheral electrodes 616 are illustrated as being in close proximity to one another, stimulating pairs may also include remote electrodes that are located on the same side of the body. Because the technique is based upon relative responses of the spinal electrodes to stimulation on each side of the body, it is preferred that a pair of stimulating peripheral electrodes 616 on one side of the body is mirrored by a corresponding pair on the other side of the body. While two corresponding pairs of stimulating peripheral electrodes are illustrated, additional pairs may also be employed. Moreover, peripheral electrodes on the same side of the body may be used in different paired combinations.

The spinal monitoring version of the physiological midline determination operates on the principle that stimulation of selected peripheral electrodes 616 causes sensory neurons to "fire," which results in changes in the neurons' membrane potential over a short period of time, causing the propagation of an electrical signal towards the brain. The induced response propagates through a chain of neurons at a rate of approximately 40 to 100 meters per second through nerve fibers on the same side of the body as the stimulation point into the spinal column and to the brain. Thus, at a certain time after the stimulation (based on the propagation rate), electrodes positioned along spinal nerves (e.g., spinal electrodes 16) observe the propagating signal (called an evoked compound action potential, or ECAP). Because there is a lateral nature to the propagation of action potentials, a spinal electrode 16 positioned closer to the side of the body on which stimulation occurs (i.e., on the same side of the physiological midline) will experience a greater response than an electrode on an opposite side of the physiological midline. Therefore, the responses of the spinal electrodes 16 to peripheral stimulation at different lateral positions can be analyzed to determine their positions with respect to the physiological midline. Note that the peripheral electrodes 616 must be positioned in a location such that stimulation induces a signal that propagates past the location of the spinal electrodes 16. For example, spinal electrodes placed in the lower back (i.e., proximate to the lumbar and/or sacral nerves) would not observe an ECAP signal caused by stimulation on an arm because such a signal would propagate through a spinal nerve towards the brain (i.e., "downstream") from the spinal electrodes 16.

Initially, a selected pair of peripheral electrodes 616 (such as $L_1$ and $L_2$, for example) is stimulated at a starting amplitude, and the ECAP response at each of the spinal electrodes 16 is recorded. This process is repeated at increasing amplitude levels until sufficient information has been collected for each of the spinal electrodes (e.g., until a quantifiable ECAP is recorded at each electrode) or until a safety limit is reached. ECAP responses are recorded in the same manner for each of the other peripheral electrode pairs. Once responses have been recorded for each of the stimulating pairs, the ECAP responses are quantified and evaluated to determine the lateral position (i.e., left or right of physiological midline) and relative distance from the physiological midline of each of the spinal electrodes 16. The ECAP responses can be quantified in different manners. For example, an ECAP response can be quantified based on the amplitude of its hyperpolarization phase ($A_{HP}$), the amplitude of its depolarization phase ($A_{DP}$), or the sum of those values ($A_{TOT}$). Alternatively, the ECAP signal may be rectified and quantified based on its integral. Based on the quantified ECAP values, a measure of each spinal electrode 16's relative position with respect to the physiological midline, such as the left/right ratio value 1108, can be calculated in ways that are analogous to those described above with respect to the peripheral monitoring process. For example, a ratio such as the left/right ratio 1108 may be calculated as the sum of the quantified ECAP response values induced by stimulation of all left side peripheral electrode pairs (e.g., $L_1$ and $L_2$) over the sum of the quantified ECAP response values induced by stimulation of all right side peripheral electrode pairs (e.g., $R_1$ and $R_2$). Other ways of quantifying the relative position of a spinal electrode 16 can also be employed.

Having determined a measure of the various spinal electrodes' positions relative to a physiological midline such as ratio 1108 or a similar value, the location of the physiological midline can be computed in the same way as described above with respect to FIG. 12. That is, the known spinal electrode positions can be utilized in conjunction with the measures of the electrodes' positions relative to the physiological midline to compute locations along the physiological midline. The spinal monitoring process and the peripheral monitoring process may be utilized in combination to obtain a more accurate position of the physiological midline. For example, different measures of a spinal electrode 16's position relative to the physiological midline (e.g., ratio values 1108) may be determined from the spinal monitoring and peripheral monitoring processes and used in combination to compute the location of the physiological midline.

While various procedures have been described for computing the location of the physiological midline of a patient using measured physiological responses, the location of the physiological midline can also be determined by measurements that are recorded through interaction with the patient. For example, the patient can be asked to indicate whether and to what degree they observe a lateral or bilateral sensation as the centroid of spinal stimulation is moved through different locations. Although the physiological midline determination process has been described in the context of its use prior to full implantation of an IPG 10, the process can also be utilized after implantation of the IPG 10. Regardless of the manner in which the location of the physiological midline is determined, its location can be displayed such as over the image 402 in the GUI 94 to provide information to the patient and clinician. Additional details regarding the determination of the location of a physiological midline are described in U.S. Patent Publication No. 2017/0281958, which is incorporated herein by reference in its entirety.

Figure 14:
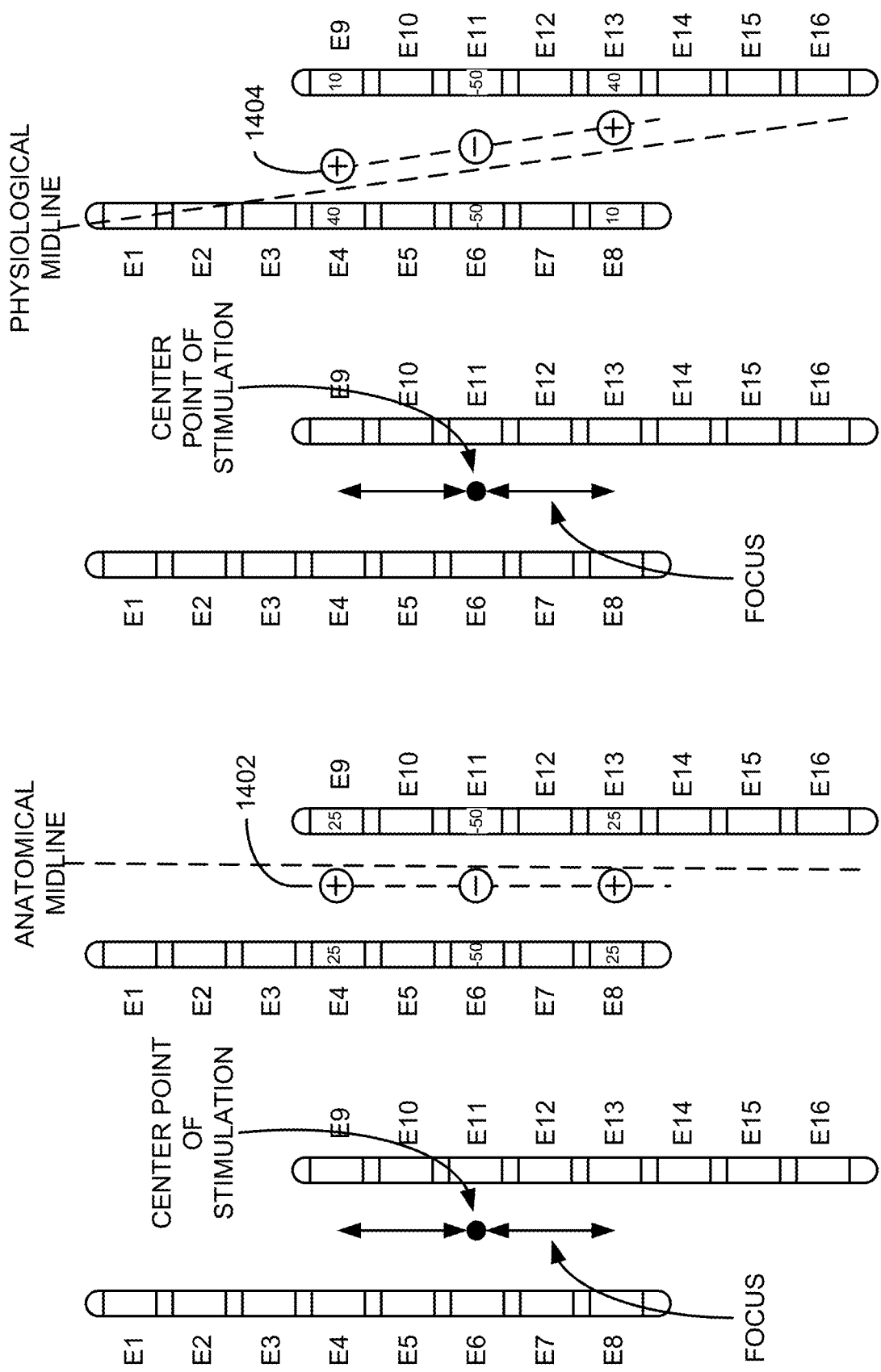
FIGS. 14A and 14B show the generation of a target stimulation field that is parallel with the anatomical midline and the physiological midline, respectively, in accordance with an example of the disclosure.

The current mapping algorithm described above can be improved in two significant ways based on the determined location of a patient's physiological midline: the target stimulation field can be constructed to lie along a line that is substantially parallel with the physiological midline and the neural element evaluation positions can be located along a line that is substantially parallel with the physiological midline. FIG. 14A shows the construction of a target stimulation field along a line 1402 that is parallel with the anatomical midline in accordance with the present current mapping algorithm. As described above, the user specifies a center point of stimulation and a focus. As FIG. 14A shows, based on these inputs, the present current mapping algorithm models the electric potentials that would be generated as a result of stimulation at a 100% cathode located at the specified center point and two equal (50%) anodes that are located at the specified focus distance directly above and below (i.e., parallel with the anatomical midline) the cathode. Given the locations of the physical electrodes, the target stimulation field is best represented when 25% of the anodic current is allocated to each of electrodes E4, E8, E9, and E13 and 50% of the cathodic current is allocated to each of electrodes E6 and E11.

When the user specifies a center point of stimulation and focus, however, the user is indicating a desired location and breadth of stimulation along or substantially parallel with the physiological midline. That is, the center point of stimulation is intended to specify an offset from the physiological midline and the focus is intended to specify the breadth of the stimulation field along a path that is substantially parallel with the physiological midline. Based on the known location of the physiological midline, the specified center point of stimulation and focus can be utilized to determine an electrode configuration that causes the stimulation field to be substantially parallel with the physiological midline, which more closely matches the user's intent. FIG. 14B shows the construction of a target stimulation field along a line 1404 that is parallel with the physiological midline in accordance with an improved current mapping algorithm. As illustrated in FIG. 14B, the specified center point of stimulation and focus are the same as in FIG. 14A. However, based on the known location of the physiological midline, the improved current mapping algorithm models the electric potentials that would be generated as a result of stimulation at a 100% cathode located at the specified center point and two equal (50%) anodes that are located at the specified focus distance away from the cathode along a line 1404 having the same slope as the physiological midline. The physiological midline can be represented by an equation in a two-dimensional coordinate system as described above, so its slope is known. Therefore, determining the location of the target anodes involves the simple calculation of the points that are the specified focus distance from the cathode along a line that intersects the cathode and has the same slope as the physiological midline. As illustrated in FIG. 14B, the changes to the target stimulation field result in a different allocation of current among the electrodes than that in FIG. 14A. Specifically, the target stimulation field that is modeled by the improved current mapping algorithm is best represented when 40% of the anodic current is allocated to each of electrodes E4 and E13, 10% of the anodic current is allocated to each of electrodes E8 and E9, and 50% of the cathodic current is allocated to each of electrodes E6 and E11. Therefore, the improved current mapping algorithm provides a different allocation of current among electrodes that more closely represents the intended stimulation field. The determined electrode configuration, which can specify a polarity and magnitude of stimulation for the electrodes (e.g., a stimulation magnitude for the utilized electrodes or a total stimulation amplitude and an allocation fraction for the utilized electrodes) can be communicated to the neurostimulator (e.g., to the IPG 10 or ETS 70 via communication link 92) to enable the neurostimulator to generate the stimulation field.

Figure 15:
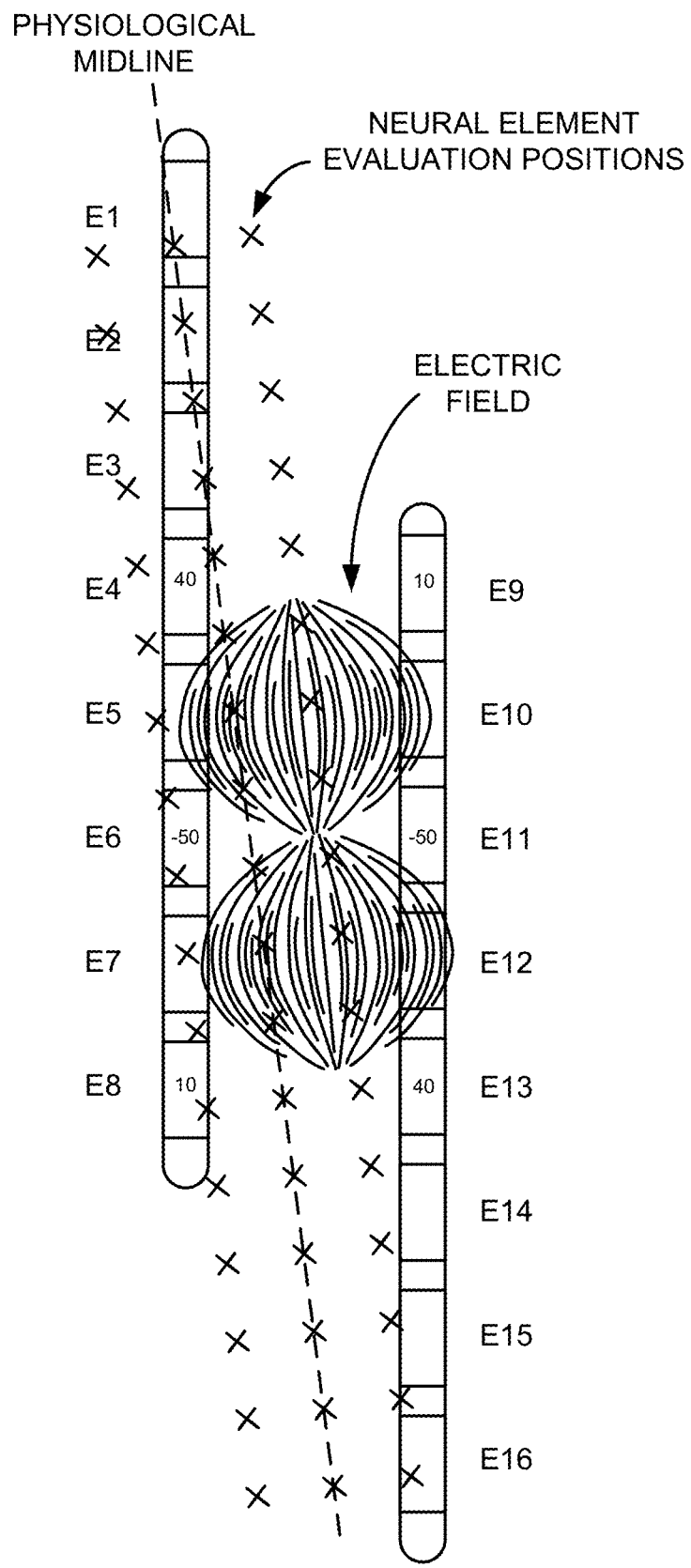
FIG. 15 shows the evaluation of the responses of neural elements to a modeled stimulation field at evaluation positions that are parallel with the physiological midline in accordance with an example of the disclosure.

In addition to constructing the target field along a line that is substantially parallel with the determined physiological midline, the neural element evaluation positions are also rotated such that they are substantially parallel with the physiological midline as illustrated in FIG. 15. Rotation of the neural element evaluation positions in accordance with the determined physiological midline aligns the evaluation positions with the dorsal column fibers upon which the neural element model is based. As a result, the volume of activation can be more accurately determined.

Figure 16:
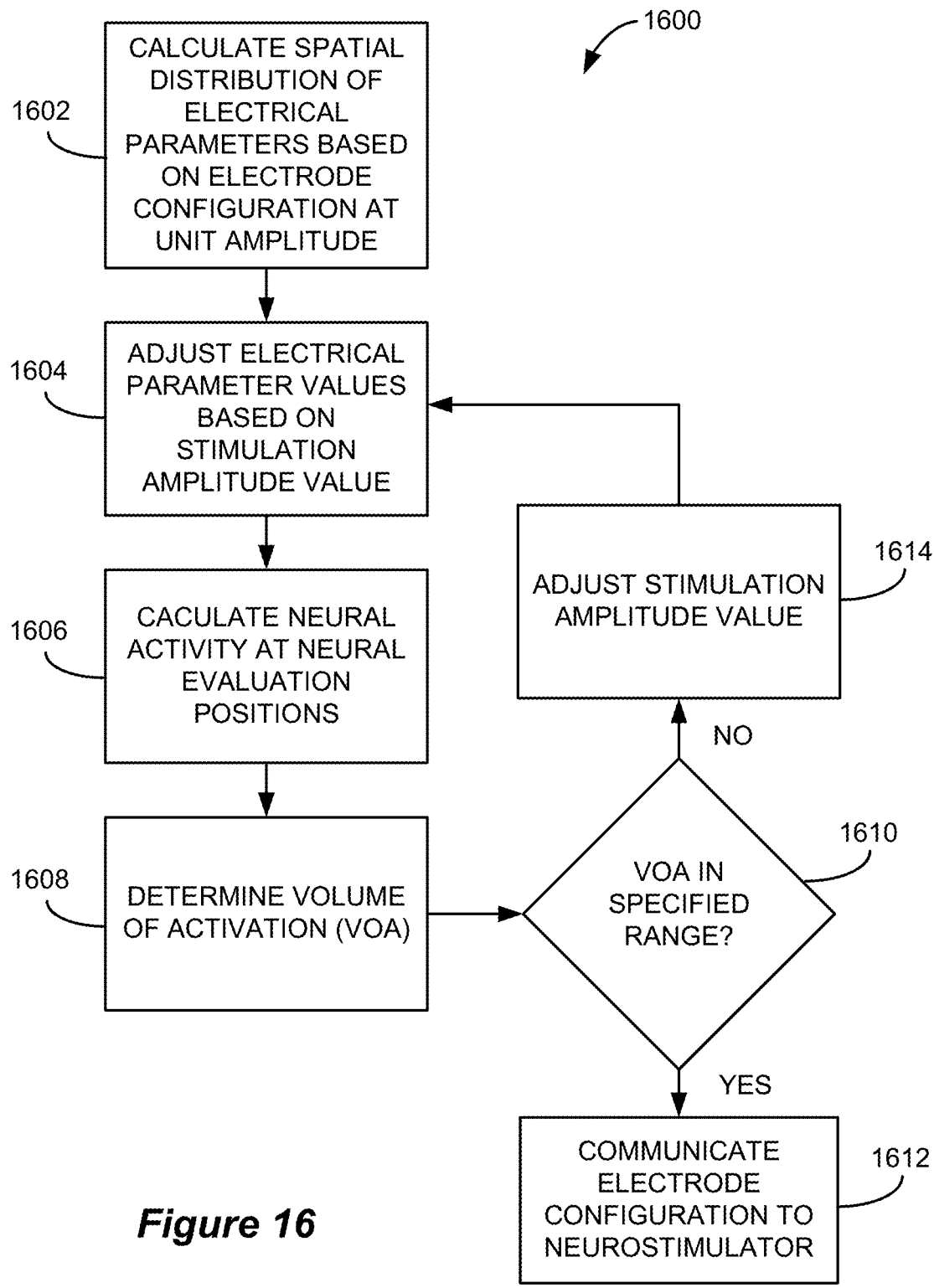
FIG. 16 is a flowchart that shows a process for maintaining a stimulation intensity that utilizes neural element modeling at evaluation positions that are parallel with the physiological midline in accordance with an example of the disclosure.

FIG. 16 is a flowchart that illustrates an improved stimulation amplitude adjustment process. The stimulation amplitude adjustment process 1600 is performed after the determination of the electrode configuration, and the electric field model that was described above is used to calculate the spatial distribution of electrical parameters (e.g., electric potentials, electric field strength, current density, etc.) based on stimulation using the determined electrode allocation at unit amplitude (e.g., 1 mA) (1602). FIG. 15 illustrates an example of the electric field that is generated using the illustrated electrode allocation (which matches the electrode allocation described with respect to FIG. 14B). The modeled electrical parameters are then adjusted from the unit amplitude base values according to the stimulation amplitude value (1604). Initially, the stimulation amplitude value may be the present stimulation amplitude setting that is being used (e.g., 5.0 mA). The electrical parameter values may be assumed to scale linearly with increasing amplitude and thus the values determined for unit current may be multiplied by a scaling factor as opposed to repeating the electric field modeling for the new stimulation amplitude.

The response to stimulation is then evaluated at several neural element evaluation positions (1606). As described above, the neural element evaluation positions are substantially parallel with the determined physiological midline as illustrated in FIG. 15. The neural element evaluation positions are substantially parallel with the physiological midline in that they are arranged in one or more lines or paths that are substantially parallel with the physiological midline. In an embodiment, the neural element evaluation positions are arranged in a grid that is centered on the physiological midline. As described above with respect to the rotation of the desired electric field, the neural element evaluation positions may be rotated to match the known slope of the physiological midline.

The electrical parameters at each of the neural element evaluation positions are input to a neural element model that estimates the response to the stimulation of neural elements positioned at the evaluation position. In one embodiment, the neural element model takes into account the morphological and electrical properties of various neural elements to estimate the response of the neural elements to electrical stimulation. The neural element model may estimate the transmembrane potentials (and/or other related parameters) that would be induced in the neural elements as a result of the modeled electric potential field. Neural activation may be determined based on an activating function (i.e., the $2^{nd}$ spatial derivative of the electrical potentials along an axis of the neural elements (which axis is parallel with the physiological midline), a driving function (i.e., a weighted average of the activating function at a node of Ranvier and those at adjacent nodes along the neural elements), or a $1^{st}$ spatial derivative of the electrical potentials along an axis of the neural elements. Neural activation may also be evaluated using a priori machine learning techniques. Based on the results of the neural model as applied at each of the neural element evaluation positions, the quantity of neural elements that would be activated (or the volume of activation) can be determined (1608).

It is then determined whether the volume of activation is within a specified range (1610). The specified range may be a range that encompasses a volume of activation that was determined to be acceptable for the patient (e.g., the volume of activation that is associated with an initial acceptable set of stimulation parameters). If the volume of activation is within the specified range, the electrode configuration is communicated from the CP computer 202 to the neurostimulator (e.g., the IPG 10 or ETS 70 via communication link 92) such that stimulation in accordance with the specified parameters may be delivered to the patient (1612). If, however, the modeled response of neural elements deviates from a desired response (i.e., the volume of activation is not within the specified range), the stimulation amplitude is either increased or decreased to bring the volume of activation towards the specified range (1614). In one embodiment, the stimulation amplitude value is increased by a fixed percentage of the present value. In another embodiment, the magnitude of the stimulation amplitude value adjustment is determined based on the difference between the determined volume of activation and the specified range. The modeled electrical parameter values are then updated based on the adjusted stimulation amplitude (1604) and the process continues iteratively until the volume of activation is determined to be within the specified range.

Figure 17:
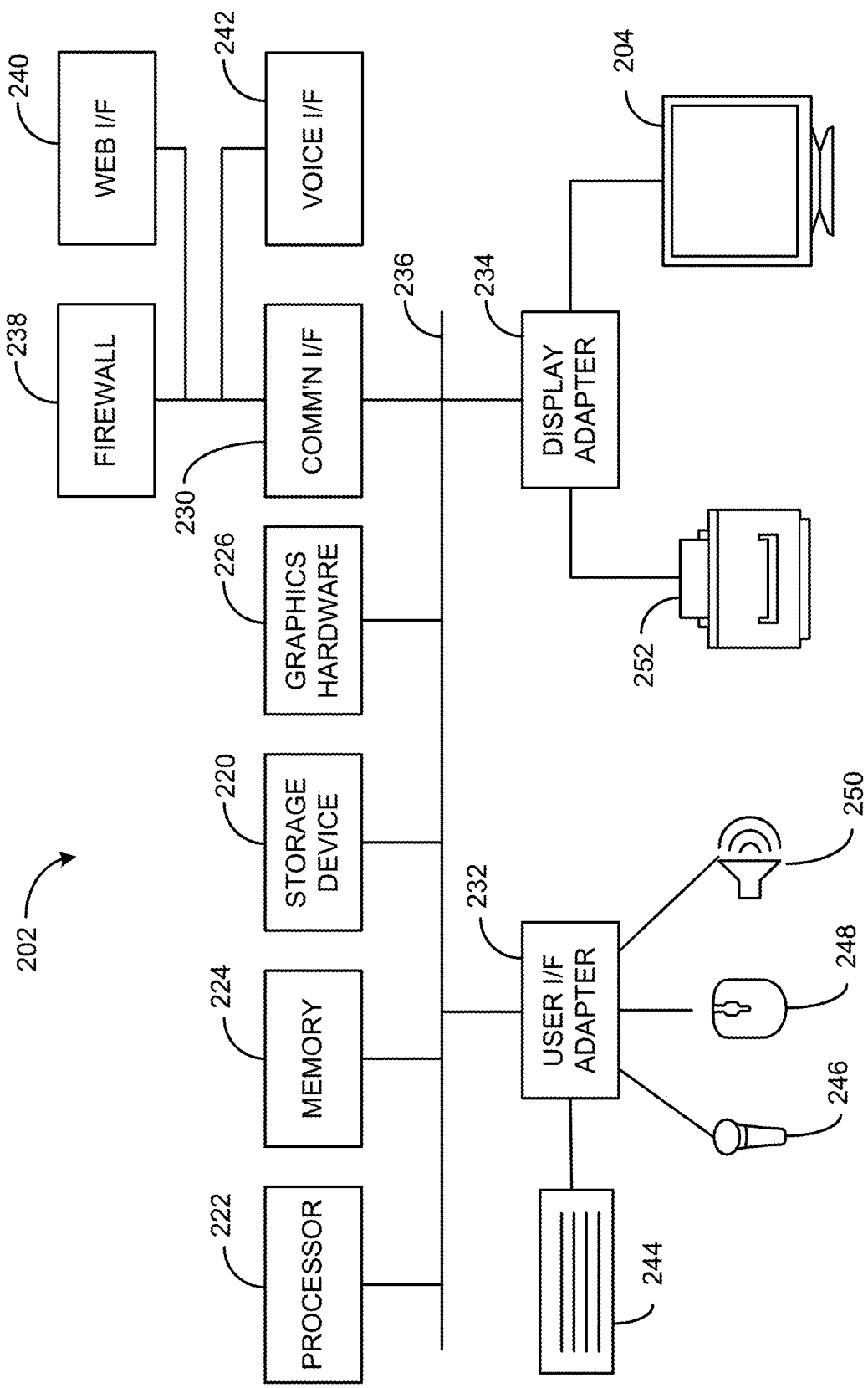
FIG. 17 shows a representative computing environment in which aspect of the disclosed technique may be executed.

FIG. 17 illustrates the various components of an example CP computer 202 that may be configured to execute CP software 96. The CP computer 202 can include the processor 222, memory 224, storage 220, graphics hardware 226, communication interface 230, user interface adapter 232 and display adapter 234—all of which may be coupled via system bus or backplane 236. Memory 224 may include one or more different types of media (typically solid-state) used by the processor 222 and graphics hardware 226. For example, memory 224 may include memory cache, read-only memory (ROM), and/or random access memory (RAM). Storage 220 may store media, computer program instructions or software (e.g., CP software 96), preference information, device profile information, and any other suitable data. Storage 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. Memory 224 and storage 220 may be used to tangibly retain computer program instructions or code organized into one or more modules and written in any desired computer programming language. As will be understood, the CP software 96 may be stored on a medium such as a CD or a USB drive, pre-loaded on a computing device such as the CP computer 202, or made available for download from a program repository via a network connection. Communication interface 230 (which may comprise, for example, the ports 206 or 208) may be used to connect the CP computer 202 to a network. Communications directed to the CP computer 202 may be passed through a protective firewall 238. Such communications may be interpreted via web interface 240 or voice communications interface 242. Illustrative networks include, but are not limited to: a local network such as a USB network; a business' local area network; or a wide area network such as the Internet. User interface adapter 232 may be used to connect a keyboard 244, microphone 246, pointer device 248, speaker 250 and other user interface devices such as a touch-pad and/or a touch screen (not shown). Display adapter 234 may be used to connect display 204 and printer 252. Processor 222 may include any programmable control device. Processor 222 may also be implemented as a custom designed circuit that may be embodied in hardware devices such as application specific integrated circuits (ASICs) and field programmable gate arrays (FPGAs). The CP computer 202 may have resident thereon any desired operating system.

While the above process has been described in terms of its performance on a CP computer 202, it will be understood that the process can also be performed on a different type of device such as the remote controller 40. In addition, various portions of the described process can be performed on the neurostimulator itself. In such an arrangement, the different type of device or the neurostimulator may include various ones of the components described with respect to FIG. 17 to perform the process.

While the target stimulation field has been described as being represented by a linear tripole, it will be understood that other field types are also possible. For example, the center point of stimulation and focus can be used to specify a target bipole in which the center point of stimulation lies at the midpoint between the target cathode and target anode, which are the specified focus distance apart. Moreover, the user inputs may include additional or different parameters and the target field may include different numbers of target poles that enable the target field to be further customized. As will be understood, the types of target fields that might be created are essentially limitless. Regardless of the type, however, the target field can be created to be substantially parallel with the physiological midline. In this regard, the target field may be considered to be substantially parallel with the physiological midline when an axis that is aligned with all of the target poles or about which the target poles are symmetrical is substantially parallel with the physiological midline. As used herein, the term parallel is intended to encompass a line or curve that lies directly on the physiological midline.

While the target field construction process is described above in terms of determining an electrode configuration that causes the stimulation field to be substantially parallel with the physiological midline, it will be understood that this refers to the attempt to determine an electrode configuration that best matches a target field that is substantially parallel with the physiological midline. The locations of the physical electrodes may not enable the resulting stimulation field to be perfectly parallel with the physiological midline.

While the target field and neural element evaluation positions have been described as being substantially parallel with a linear physiological midline, the physiological midline need not be represented as a single line. For example, the physiological midline may be represented by multiple line segments or a curve. In such a case, the target field and neural element evaluation positions can be arranged to be substantially parallel with the non-linear path of the physiological midline.

While the invention herein disclosed has been described by means of specific embodiments and applications thereof, numerous modifications and variations could be made thereto by those skilled in the art without departing from the scope of the invention set forth in the claims.

What is claimed is:

1. A system, comprising:
    a neurostimulator that is connectable to a plurality of electrodes that are implantable in a patient; and
    an external device that is configured to:
        determine a location of a physiological midline of the patient based on measurements associated with one or more of the plurality of electrodes;
        receive one or more inputs that are associated with a desired location of a stimulation field that is to be generated by the neurostimulator;
        determine an electrode configuration that causes the stimulation field to be substantially parallel with the physiological midline;
        communicate the electrode configuration to the neurostimulator;
        determine an equation in a two-dimensional coordinate system that describes the location of the physiological midline,
        model an electric field that would result from stimulation using the electrode configuration;
        determine a plurality of neural element evaluation positions that are substantially parallel with the physiological midline based on the equation;
        model a response of neural elements to the modeled electric field at the plurality of neural element evaluation positions; and
        adjust the electrode configuration when the modeled response of neural elements deviates from a desired response.

2. The system of claim 1, wherein the external device is configured to determine the physiological midline by measuring one or more responses at one or more peripheral electrodes to electrical stimulation using the one or more of the plurality of electrodes.

3. The system of claim 1, wherein the external device is configured to determine the physiological midline by measuring one or more responses at the one or more of the plurality of electrodes to electrical stimulation using one or more peripheral electrodes.

4. The system of claim 1, wherein the one or more inputs comprise a center point of the stimulation field.

5. The system of claim 1, wherein the one or more inputs comprise a focus of the stimulation field.

6. The system of claim 1, wherein the external device is configured to determine an electrode configuration that causes the stimulation field to be substantially parallel with the physiological midline by:
    determining a location of one or more target poles based on the one or more inputs, wherein the target poles are aligned with or symmetrical about an axis that is substantially parallel with the physiological midline;
    modeling an electric field that would result from stimulation at the one or more target poles; and
    determining the electrode configuration that corresponds to the modeled electric field.

7. The system of claim 6, wherein the one or more target poles comprise a target cathode at a center point of the stimulation field and two equal target anodes that are each positioned at an equal distance from the center point of stimulation.

8. The system of claim 1, wherein the electrode configuration specifies a polarity and magnitude of stimulation for the plurality of electrodes.

9. The system of claim 1, wherein the external device is configured to adjust the electrode configuration by adjusting an amplitude of stimulation that is provided at the plurality of electrodes.

10. An external device that is configured to communicate with a neurostimulator, comprising control circuitry that is configured to:
    determine a location of a physiological midline of a patient based on measurements associated with one or more of a plurality of electrodes that are connectable to the neurostimulator and implantable in the patient;
    receive one or more inputs that are associated with a desired location of a stimulation field that is to be generated by the neurostimulator;
    determine an electrode configuration that causes the stimulation field to be substantially parallel with the physiological midline;
    communicate the electrode configuration to the neurostimulator;
    determine an equation in a two-dimensional coordinate system that describes the location of the physiological midline,
    model an electric field that would result from stimulation using the electrode configuration;
    determine a plurality of neural element evaluation positions that are substantially parallel with the physiological midline based on the equation;
    model a response of neural elements to the modeled electric field at the plurality of neural element evaluation positions; and
    adjust the electrode configuration when the modeled response of neural elements deviates from a desired response.

11. The external device of claim 10 wherein the one or more inputs comprise a center point of the stimulation field.

12. The external device of claim 10, wherein the one or more inputs comprise a focus of the stimulation field.

13. The external device of claim 10, wherein the external device is configured to determine an electrode configuration that causes the stimulation field to be substantially parallel with the physiological midline by:
    determining a location of one or more target poles based on the one or more inputs, wherein the target poles are aligned with or symmetrical about an axis that is substantially parallel with the physiological midline;
    modeling an electric field that would result from stimulation at the one or more target poles; and
    determining the electrode configuration that corresponds to the modeled electric field.

14. The external device of claim 13, wherein the one or more target poles comprise a target cathode at a center point of the stimulation field and two equal target anodes that are each positioned at an equal distance from the center point of stimulation.

15. The external device of claim 10, wherein the electrode configuration specifies a polarity and magnitude of stimulation for the plurality of electrodes.

16. The external device of claim 10, wherein the external device is configured to adjust the electrode configuration by adjusting an amplitude of stimulation that is provided at the plurality of electrodes.

17. A method for providing electrical stimulation to the spinal cord of a patient using a neurostimulator and one or more of a plurality of electrodes connected to the neurostimulator and implanted in the patient and an external device that is configured to communicate with the neurostimulator, the method comprising:

using the external device:
- determining a location of a physiological midline of the patient based on measurements associated with the one or more of the plurality of electrodes;
- receiving one or more inputs that are associated with a desired location of a stimulation field that is to be generated by the neurostimulator;
- determining an electrode configuration that causes the stimulation field to be substantially parallel with the physiological midline;
- determining an equation in a two-dimensional coordinate system that describes the location of the physiological midline,
- modeling an electric field that would result from stimulation using the electrode configuration;
- determining a plurality of neural element evaluation positions that are substantially parallel with the physiological midline based on the equation;
- modeling a response of neural elements to the modeled electric field at the plurality of neural element evaluation positions;
- adjusting the electrode configuration when the modeled response of neural elements deviates from a desired response, and
- communicating the electrode configuration to the neurostimulator.

18. The method of claim 17, wherein determining the physiological midline comprises measuring one or more responses at one or more peripheral electrodes to electrical stimulation using the one or more of the plurality of electrodes.

19. The method of claim 17, wherein determining the physiological midline comprises measuring one or more responses at the one or more of the plurality of electrodes to electrical stimulation using one or more peripheral electrodes.

20. The method of claim 17, wherein determining an electrode configuration that causes the stimulation field to be substantially parallel with the physiological midline comprises:
- determining a location of one or more target poles based on the one or more inputs,
- wherein the target poles are aligned with or symmetrical about an axis that is substantially parallel with the physiological midline;
- modeling an electric field that would result from stimulation at the one or more target poles; and
- determining the electrode configuration that corresponds to the modeled electric field.

* * * * *